(12) United States Patent
Ziv et al.

(10) Patent No.: US 8,888,676 B2
(45) Date of Patent: *Nov. 18, 2014

(54) FEMALE URINARY INCONTINENCE DEVICES

(75) Inventors: Elan Ziv, Ramat-Gan (IL); Amir Perle, Haifa (IL); Elisheva Sabo, Herzlia (IL); Idan Bauder, Carmiel (IL)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 13/534,122

(22) Filed: Jun. 27, 2012

(65) Prior Publication Data

US 2012/0271099 A1   Oct. 25, 2012

Related U.S. Application Data

(63) Continuation of application No. 12/365,965, filed on Feb. 5, 2009, now Pat. No. 8,449,446.

(60) Provisional application No. 61/006,927, filed on Feb. 6, 2008.

(51) Int. Cl.
  *A61F 2/00* (2006.01)
(52) U.S. Cl.
  CPC ......... *A61F 2/0009* (2013.01); *A61F 2250/001* (2013.01); *A61F 2250/0039* (2013.01)
  USPC ......................................................... 600/29
(58) Field of Classification Search
  USPC ...................... 600/29–32; 128/885
  See application file for complete search history.

(56) References Cited

U.S. PATENT DOCUMENTS

| | | |
|---|---|---|
| 4,139,006 A | 2/1979 | Corey |
| 4,823,814 A | 4/1989 | Drogendijk et al. |
| 4,920,986 A | 5/1990 | Biswas |
| 5,007,894 A | 4/1991 | Enhorning |
| 5,036,867 A | 8/1991 | Biswas |
| 5,386,836 A | 2/1995 | Biswas |
| 5,483,976 A | 1/1996 | McLaughlin et al. |
| 5,609,559 A | 3/1997 | Weitzner |
| 5,618,256 A | 4/1997 | Reimer |

(Continued)

FOREIGN PATENT DOCUMENTS

| | | |
|---|---|---|
| GB | 1115727 | 5/1968 |
| GB | 2364645 | 2/2002 |

(Continued)

OTHER PUBLICATIONS

Applicant-Initiated Interview Summary Dated Nov. 29, 2012 From the US Patent and Trademark Office Re. U.S. Appl. No. 12/365,965.

(Continued)

*Primary Examiner* — Christine Matthews
(74) *Attorney, Agent, or Firm* — Kimberly-Clark Worldwide, Inc.

(57) ABSTRACT

Disclosed is a female urinary incontinence-inhibiting device comprising a flexible torus including at least one slot configured to, under compression, flexibly reduce the outer diameter of the flexible torus, the flexible torus having a diameter configured to inhibit female urinary incontinence when placed in a vagina and a stabilizing element, coupled to the flexible torus, the stabilizing element having a size and position configured to stabilize the flexible torus within the vagina.

10 Claims, 22 Drawing Sheets

(56) References Cited

U.S. PATENT DOCUMENTS

| | | | |
|---|---|---|---|
| 5,785,640 | A | 7/1998 | Kresch et al. |
| 5,813,973 | A | 9/1998 | Gloth |
| 6,042,536 | A | 3/2000 | Tihon et al. |
| 6,090,098 | A | 7/2000 | Zunker et al. |
| 6,110,101 | A | 8/2000 | Tihon et al. |
| 6,418,930 | B1 | 7/2002 | Fowler |
| 6,530,879 | B1 | 3/2003 | Adamkiewicz |
| 6,558,370 | B2 | 5/2003 | Moser |
| 6,645,137 | B2 | 11/2003 | Ulmstein et al. |
| 6,695,763 | B2 | 2/2004 | Zunker et al. |
| 6,739,340 | B1 | 5/2004 | Jensen et al. |
| 6,770,025 | B2 | 8/2004 | Zunker |
| 8,449,446 | B2 * | 5/2013 | Ziv et al. .......................... 600/29 |
| 2004/0084054 | A1 * | 5/2004 | Kaseki et al. .................. 128/885 |
| 2004/0249238 | A1 | 12/2004 | Farrell |
| 2007/0203429 | A1 | 8/2007 | Ziv |
| 2008/0119688 | A1 * | 5/2008 | Robert et al. .................... 600/31 |
| 2009/0203959 | A1 * | 8/2009 | Ziv et al. .......................... 600/29 |

FOREIGN PATENT DOCUMENTS

| | | |
|---|---|---|
| WO | WO 88/10106 | 12/1988 |
| WO | WO 98/49980 | 11/1998 |
| WO | WO 01/67983 | 9/2001 |
| WO | WO 2004/103213 | 12/2004 |
| WO | WO 2008/152628 | 12/2008 |

OTHER PUBLICATIONS

Advisory Action Before the Filing of an Appeal Brief Dated Jul. 2, 2012 From the US Patent and Trademark Office Re. U.S. Appl. No. 12/365,965.
Letter From PRTSI, Inc. Dated Dec. 14, 2010 to U.S. Appl. No. 12/365,965. References Material to Patentability of U.S. Appl. No. 12/365,965.
Official Action Dated Oct. 4, 2011 From the US Patent and 'trademark Office Re. U.S. Appl. No. 12/365,965.
Official Action Dated Dec. 15, 2011 From the US Patent and Trademark Office Re. U.S. Appl. No. 12/365,965.
Official Action Dated Mar. 27, 2012 From the US Patent and Trademark Office Re. U.S. Appl. No. 12/365,965.
Response Dated Dec. 5, 2011 to Official Action of Oct. 4, 2011 From the US Patent and Trademark Office Re. U.S. Appl. No. 12/365,965.
Thyssen et al. "A New Intravaginal Device for Stress Incontinence in Women", BJU International, 88: 889-892, Sep. 1, 2001.
Viera et al. "Practical Use of the Pessary", American Family Physician, 61(9): 2719-2726, 2729, May 1, 2000.
Official Action Dated Sep. 17, 2012 From the US Patent and Trademark Office Re. U.S. Appl. No. 12/365,965.

* cited by examiner

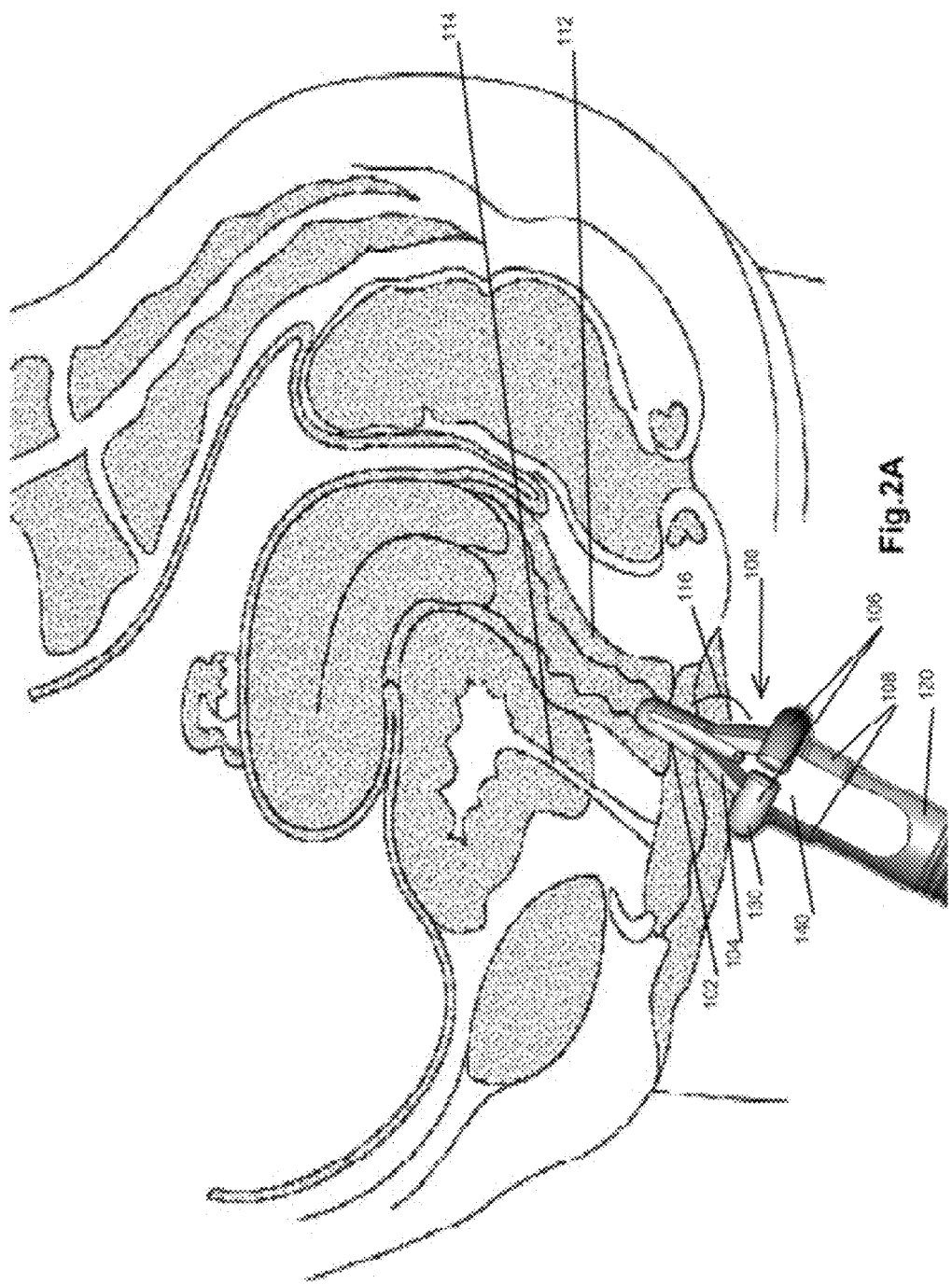

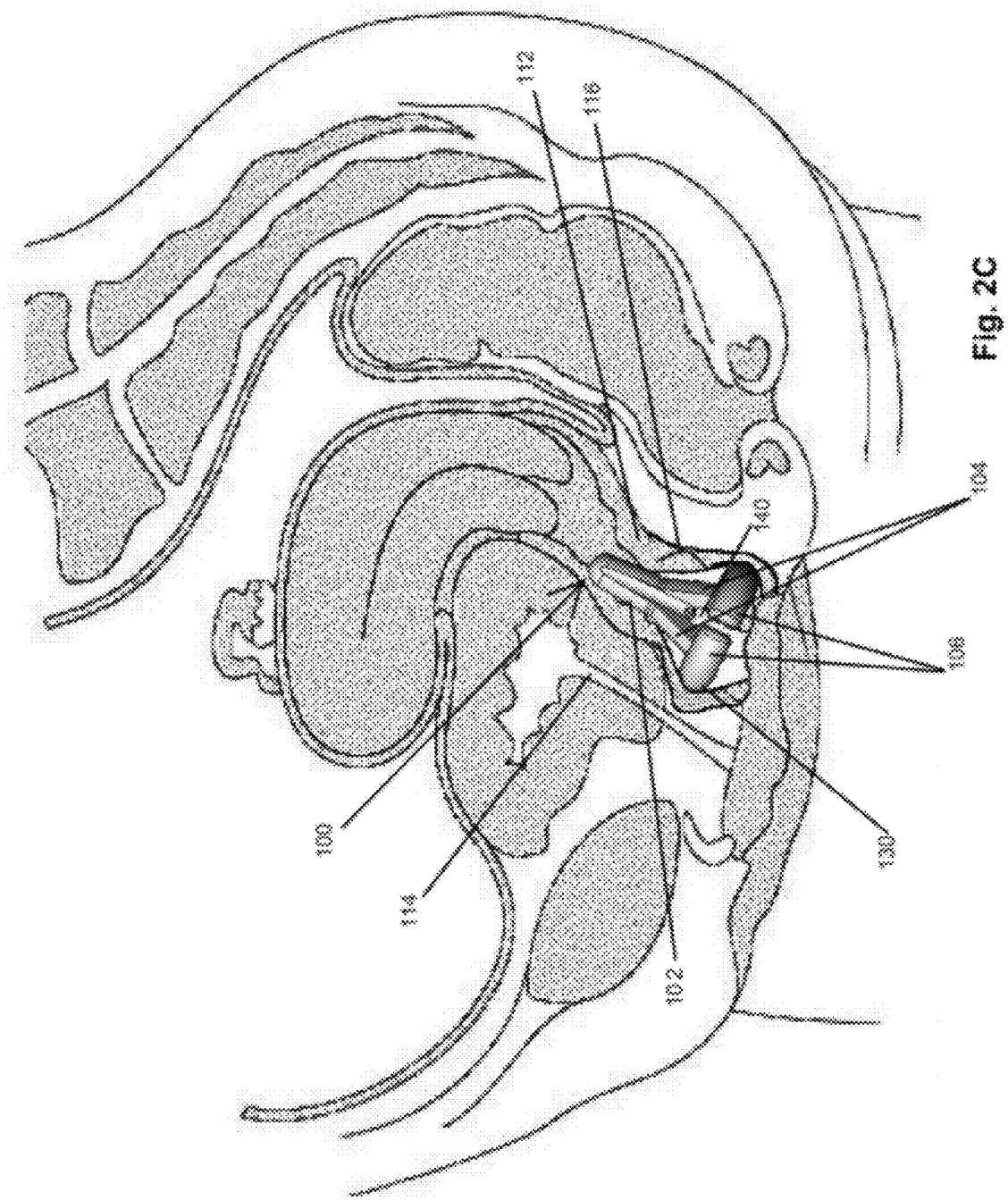

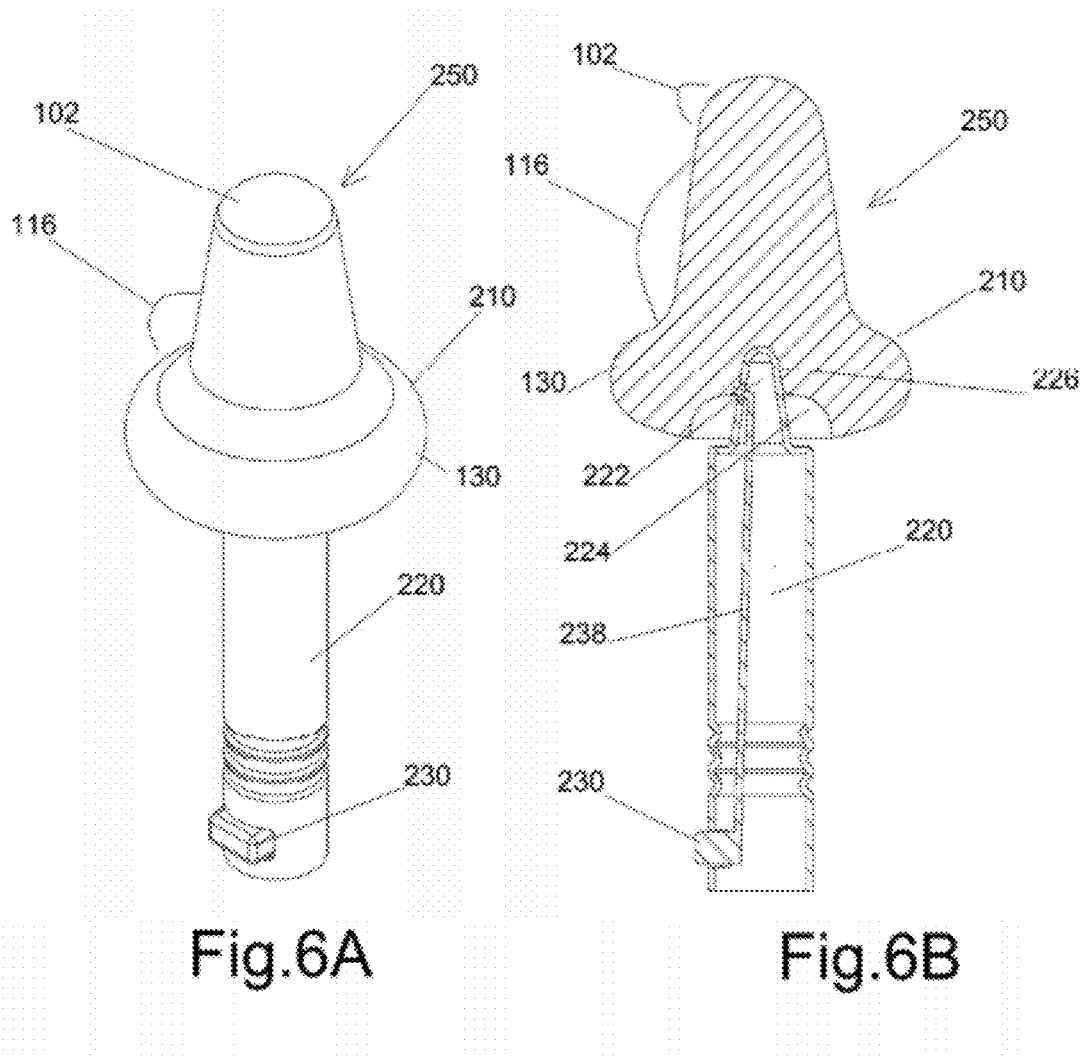

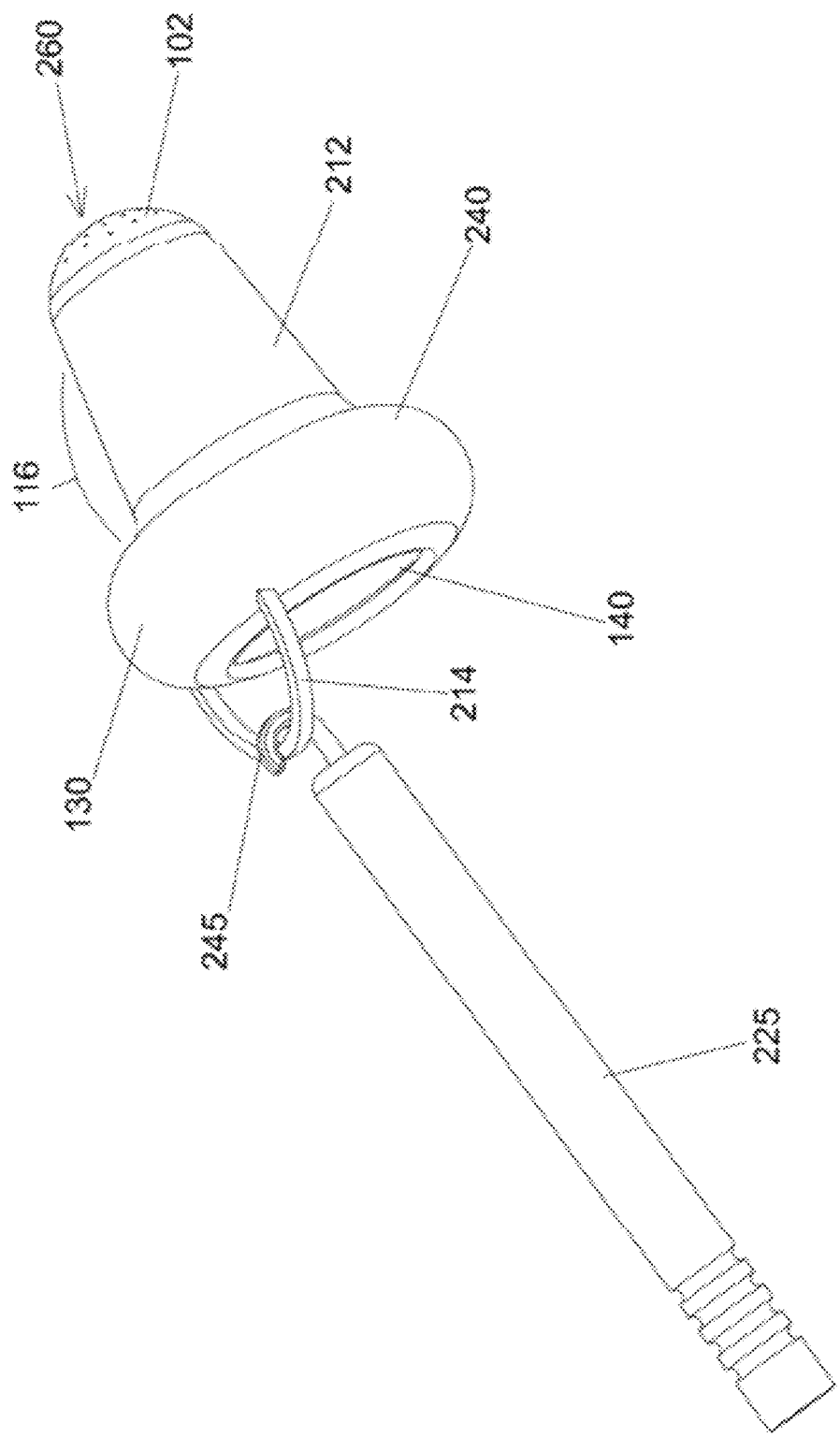

FEMALE URINARY INCONTINENCE DEVICES

RELATED APPLICATIONS

This application is a continuation of U.S. patent application Ser. No. 12/365,965 filed on Feb. 5, 2009, which claims the benefit under 35 USC 119(e) of U.S. Provisional Patent Application No. 61/006,927 filed on Feb. 6, 2008. The contents of all of the above applications are incorporated by reference as if fully set forth herein.

FIELD AND BACKGROUND OF THE INVENTION

The present invention, in some embodiments thereof, relates to devices and methods for treating female urinary incontinence and, more particularly but not exclusively, to female incontinence treatment kits including devices that aid in inserting and/or removing female urinary incontinence devices.

Female stress urinary incontinence, the involuntarily loss of urine, may occur during normal movements including laughing, coughing, sneezing, exercise and any physical activity that causes an increase in intra-abdominal pressure to cause inappropriate opening of the urethra.

Inappropriate opening of the urethra is related to weakened muscles and pelvic tissues that are unable to adequately support the urethra in its correct position and may result from repetitive straining of the pelvic muscles, childbirth, and loss of pelvic muscle tone.

Female stress urinary incontinence is embarrassing and unpredictable, causing afflicted women to avoid many common activities and even social situations.

Devices which insert into the vagina to press against the bladder neck and the urethra and control incontinence are known. Vaginally inserted devices are normally prescribed and fitted by a health care professional and require regular visits to a health care professional for assessment.

US Patent Publication 2004/0249238 (Farrell) teaches an incontinence inhibiting device having a solid handle and solid round base and is hereby included by reference as if fully disclosed herein.

SUMMARY OF THE INVENTION

According to an aspect of some embodiments of the present invention there is provided a female urinary incontinence-inhibiting device comprising a flexible torus including at least one slot configured to, under compression, flexibly reduce the outer diameter of the flexible torus, the flexible torus having a diameter configured to inhibit female urinary incontinence when placed in a vagina and a stabilizing element, coupled to the flexible torus, the stabilizing element having a size and position configured to stabilize the flexible torus within the vagina.

In some embodiments of the invention, the stabilizing element comprises at least two flexible posts.

In some embodiments of the invention, the at least two flexible posts are symmetrically arranged around the flexible torus.

In some embodiments of the invention, the at least two flexible posts are flexibly joined.

In some embodiments of the invention, the stabilizing element includes a channel through which a string extends.

In some embodiments of the invention, the flexible torus includes spokes forming a channel through which the string passes.

In some embodiments of the invention, the flexible torus includes spokes forming a receptacle and the string includes a coupling end that removably attaches to the receptacle.

In some embodiments of the invention, the device is included in a kit including an insertion handle having at least two connectors configured to removably connect to the flexible torus.

In some embodiments of the invention, a downward surface of the flexible torus includes a downwardly projecting ring.

In some embodiments of the invention, the device is included in a kit including a handle having a hook, the hook configured to removably surround at least a portion of the downwardly projecting ring.

In some embodiments of the invention, the downwardly projecting ring is off-center to a longitudinal axis running through the stabilizing element.

In some embodiments of the invention, the device is included in a kit including a handle having a hook, the hook configured to removably surround at least a portion of the downwardly projecting ring.

In some embodiments of the invention, the device includes an elongate receptacle parallel to a longitudinal axis of the stabilizing element, the elongate receptacle configured to be slidingly loaded onto an elongate insertion handle.

In some embodiments of the invention, the device is included in a kit including an insertion tube having an elongate tip configured to slide into the elongate receptacle.

In some embodiments of the invention, the kit additionally includes a handle having a hook configured to removably surround at least a portion of the downwardly projecting ring.

According to another aspect of some embodiments of the present invention there is provided a female urinary incontinence-inhibiting device, comprising a round element having a circumference with a diameter configured to inhibit female urinary incontinence when placed in a vagina, the round element including a coupling aperture of sufficient size to allow insertion of an average finger of a female; and stabilizing element extending from an upper surface of the round element and configured to stabilize the position of the round element within the vagina.

In some embodiments of the invention, the center of the coupling aperture is aligned with the axial axis of the round element.

In some embodiments of the invention, the center of the coupling aperture is unaligned with the axial axis of the round element.

In some embodiments of the invention, the device is included in a kit including an insertion handle having at least two connectors, each connector configured to each removably connect to the round element.

In some embodiments of the invention, the device includes a string extending downwardly from the round element.

In some embodiments of the invention, the stabilizing element includes a channel through which the string extends.

In some embodiments of the invention, the round element includes spokes forming a channel through which the string passes.

In some embodiments of the invention, the spokes form a receptacle and the string includes a coupling end that removably attaches to the receptacle.

In some embodiments of the invention, the stabilizing element comprises a wall surrounding a cavity, the cavity being contiguous with at least a portion of the coupling aperture.

In some embodiments of the invention, the device includes a ring projecting downwardly from a downward surface of the round element.

In some embodiments of the invention, the device is included in a kit including a handle having a hook, the hook configured to removably surround at least a portion of the ring.

In some embodiments of the invention, the ring is centered over a longitudinal axis running through the stabilizing element.

In some embodiments of the invention, the ring is off-center from a longitudinal axis running through the stabilizing element.

In some embodiments of the invention, the insertion element comprises a coupling tip.

According to another aspect of some embodiments of the present invention there is provided a female urinary incontinence-inhibiting device, comprising a round element having a circumference of a diameter configured to inhibit female urinary incontinence when placed in a vagina, the round element the device includes a coupling aperture of sufficient size to allow insertion of an average finger of a female; and a coupling element slidingly engaged in the coupling aperture.

In some embodiments of the invention, the device includes a stabilizing element extending from an upper surface of the round element and configured to stabilize the position of the round element within the vagina.

In some embodiments of the invention, the stabilizing element includes an elongate receptacle configured to be slidingly engaged by the coupling element.

In some embodiments of the invention, the stabilizing element includes an elongate receptacle configured to be slidingly loaded onto an elongate insertion handle.

In some embodiments of the invention, the device is included in a kit including an insertion tube having an elongate tip configured to slide into the coupling element.

In some embodiments of the invention, the device includes a ring.

In some embodiments of the invention, the kit additionally includes a handle having a hook configured to removably surround at least a portion of the ring.

In some embodiments of the invention, the stabilizing element includes a radially outwardly projecting curvature located a distance from the round element.

In some embodiments of the invention, the distance between the outwardly projecting curvature and the round element is sufficient to encourage vaginal tenting between the outwardly projecting curvature and the round element.

In some embodiments of the invention, the stabilizing element comprises at least two flexible posts.

In some embodiments of the invention, each of the at least two flexible posts include an upper prong configured for insertion into an insertion tube.

In some embodiments of the invention, the device is included in a kit including an insertion tube configured to hold each of the prongs in a compact configuration during insertion.

In some embodiments of the invention, the at least two flexible posts are joined below the radially outwardly projecting curvature.

In some embodiments of the invention, the round element comprises at least one slot configured to, under compression, flexibly reduce the outer diameter of the round element for insertion into the vagina.

In some embodiments of the invention, the round element includes a metallic receptacle configured to magnetically connect to a magnetic tip of an insertion handle.

In some embodiments of the invention, the device is included in a kit including an insertion handle having a magnetic tip configured to magnetically connect to the magnetized receptacle.

In some embodiments of the invention, the insertion handle additionally includes a connector rod configured to removably connect to the round element.

In some embodiments of the invention, the device includes a ring projecting downward from the round element, the ring being off-center to a longitudinal axis of the stabilizing element.

In some embodiments of the invention, the kit additionally includes a handle having a hook, the hook configured to removably surround at least a portion of the ring.

According to still another aspect of some embodiments of the present invention there is provided a female urinary incontinence-inhibiting device, comprising a stabilizing element comprising a cone; and a substantially solid round base connected to the wide portion of the cone, the round base having an outer diameter configured fit in a vagina and inhibit female urinary incontinence, the round base further including at least one channel therethrough, the at least one channel having an average cross section diameter sufficient to allow passage of female secretions when the device is positioned in a vagina.

In some embodiments of the invention, the at least one channel comprises a tubular passage parallel to the longitudinal axis of the cone.

In some embodiments of the invention, the at least one channel comprises a groove positioned radially around the circumference of the round base.

According to a further aspect of some embodiments of the present invention there is provided a female urinary incontinence inhibiting device comprising a round base having an outer diameter configured for insertion into the vagina and inhibiting female urinary incontinence; a stabilizing element, extending upwardly from an upward surface of the round base and configured to stabilize the position of the round base within the vagina; and a string extending downwardly from a downward surface of the round base.

In some embodiments of the invention, the stabilizing element includes a coupling projection and the string includes a looped portion configured to loop around the coupling projection.

In some embodiments of the invention, the round base includes a string receptacle and the string includes a coupling configured to removably connect to the string receptacle.

In some embodiments of the invention, the round base includes a latch configured to receive a looped portion of the string.

In some embodiments of the invention, the latch comprises a flexible post and semicircular element, the flexible post being configured to moveably connect the semicircular element.

According to another aspect of some embodiments of the present invention there is provided a female urinary incontinence inhibiting device comprising a stabilizing element; two round elements extending from the stabilizing element, comprising a first round element located a distance from a second round element, wherein the first round element has a diameter configured to inhibit female urinary incontinence when placed in a vagina.

In some embodiments of the invention, the stabilizing element extends axially with respect to the first round element.

In some embodiments of the invention, the second round element comprises a diameter configured to anchor the device in the vagina.

In some embodiments of the invention, the distance between the two round elements is sufficient to encourage vaginal tenting.

According to an additional aspect of some embodiments of the present invention there is provided a method for manufacturing a female urinary incontinence device, the method comprising forming a torus having an outer diameter configured to press radially outwardly such that, when placed in a vagina, a portion of the vagina is pressed against a portion of the urinary tract, thereby inhibiting female urinary incontinence, extending a stabilizing element axially upwardly from an upper surface of the torus, extending a ring downwardly from a lower surface of the torus, the ring being off center to the axis of the torus, forming an axial channel through a portion of the stabilizing element, and forming a rod configured to pass into the axial channel.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A, 1B, 2A, 2B and 2C show a slotted ring female urinary incontinence device, insertion devices and method for insertion, according to embodiments of the present invention;

FIGS. 6A-6B show a magnetic female urinary incontinence devices and insertion device, according to embodiments of the present invention;

FIG. 9 shows the female urinary incontinence device of FIG. 8A and an alternative removal device, according to embodiments of the present invention;

DESCRIPTION OF SPECIFIC EMBODIMENTS OF THE INVENTION

Figure 1A:
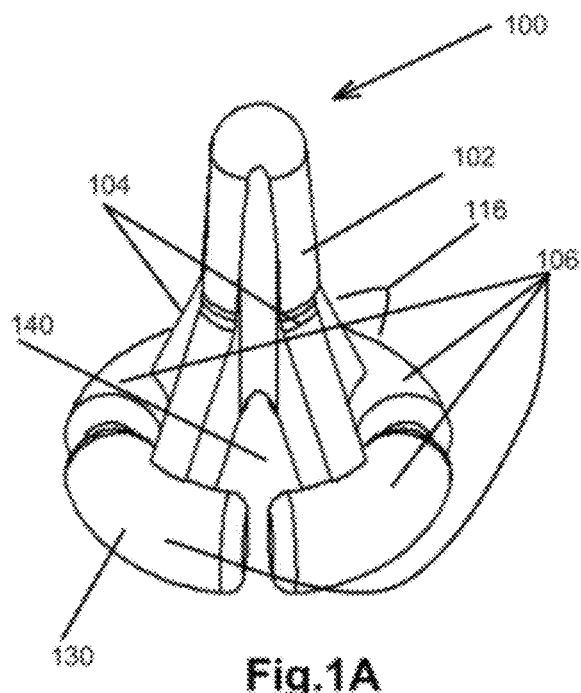

The present invention, in some embodiments thereof, relates to devices and methods for treating female urinary incontinence and, more particularly but not exclusively, to female incontinence treatment kits including devices that aid in inserting and/or removing female urinary incontinence devices.

There are thus provided configurations of female urinary incontinence devices that insert into a vagina and are configured to place pressure through the vaginal wall against a urethra, thereby inhibiting and/or preventing female urinary incontinence.

In some embodiments, the female urinary incontinence device includes a round base made up of separate multiple semi-circular sections that are connected to flexible stabilizing posts, axially extending upward from the round base and radially inward to form a cone shape.

The flexible stabilizing posts allow movement of the semi-circular sections so that the overall diameter of the round base adjusts to the space provided between the vaginal walls, thereby affording a better fit and/or greater comfort to the user during usage.

In further embodiments, the female urinary incontinence device includes a torus having a contiguous round base with a central space, thereby allowing a user to place the device on a finger during insertion.

In some embodiments, the torus configuration includes an off-center, low bulk retrieval ring, allowing easy retrieval without impeding insertion of the user finger into the device during insertion into the vagina.

In still further embodiments, secretion aiding female urinary incontinence devices are presented in which the device includes passages that allow passage of female secretions, thereby adding to user comfort.

In some configurations of secretion aiding female urinary incontinence devices, the round base includes channels allowing secretion passage. In other configurations, the round base includes grooves around the outer perimeter, forming radially outward projecting petals that maintain pressure against the vaginal walls while the grooves allow secretions to pass.

In general, the vaginal walls hug a female urinary incontinence device in a configuration often referred to as "tenting", whereby the vaginal walls form a tent-like configuration around cone and round base of the female urinary incontinence device. Presented are a variety of female urinary incontinence devices that take advantage of vaginal tenting to provide increase traction and less chance of expulsion during use.

In some embodiments, the female urinary incontinence device includes an extra ring around the cone, the extra ring providing additional traction against dislodgement.

In other embodiments, a female urinary incontinence device is presented in which stabilizing elements project from a round base. Each of the stabilizing elements include a radially outwardly projecting curvature.

The stabilizing posts contract during insertion and expand following placement. In the expanded configuration, the outward pressure of the curved post portions pressing against the tented vagina provide friction and resistance against displacement.

In further embodiments, the stabilizing elements are free standing and include upper prongs configured to insert into an insertion tube. The insertion tube is configured to hold the stabilizing elements in a compact configuration during insertion. Following insertion, the insertion tube is removed and the stabilizing elements resiliently bend radially outward to lodge in the tented vaginal walls.

In still further embodiments the stabilizing elements are adjoined just below the radially outwardly projecting curvatures so that the portions of the stabilizing elements extending upward of the adjoined portions flex radially inward during insertion.

Further embodiments of the invention include additional aids for insertion and/or removal of female urinary incontinence devices.

For example, in some embodiments, the female urinary incontinence device includes a receptacle configured to be slidingly loaded onto an elongate insertion handle. The female urinary incontinence device is included in a kit with a handle having a coupling end configured to slidingly insert into the receptacle on the female urinary incontinence device.

In still further embodiments, the female urinary incontinence device is included in a kit and is presented along with a handle having a magnetic tip. A metallic port on the female urinary incontinence device is configured to receive the magnetic tip so that during removal, the user can easily align the handle and remove the female urinary incontinence device.

In still further embodiments, a string is connected to the round base of the female urinary incontinence device to facilitate removal. In further embodiments, the string is removably connected to the round base and the user may change to a new string after every use or after several uses.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1A illustrates a female urinary incontinence device 100.

Slotted Female Urinary Incontinence Device

Female urinary incontinence device 100 including a blunt nose 102, a cone 116 comprising multiple resilient posts 104 and a round base 130 comprising multiple semi-circular sections 106 situated around a cavity 140 that facilitates easy manipulation of female urinary incontinence device 100 with a user finger.

The resilience of posts 104 allow movement of semi-circular sections 106 such that the overall diameter of round base 130 adjusts so that a user may be provided with a proper fit and/or proper comfort level by ensuring proper adjustment to vaginal dimensions.

In some embodiments there are at least two and no more than eight multiple ring sections 106, each connected to one or more posts 104.

There are many devices configured for facilitating insertion of female urinary incontinence device 100.

Insertion of Slotted Female Urinary Incontinence Device

Figure 1B:
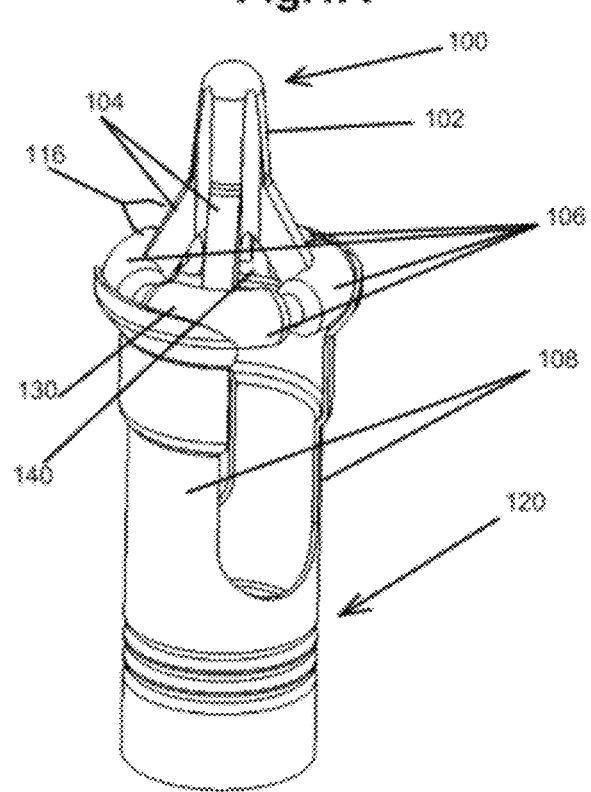

FIG. 1B shows female urinary incontinence device 100 loaded on an insertion device 120 having multiple insertion prongs 108 that grasp and stabilize round base 130. While only two insertion prongs 108 are shown, insertion device 120 is contemplated with three, four, six or even eight insertion prongs 108.

Figure 2B:
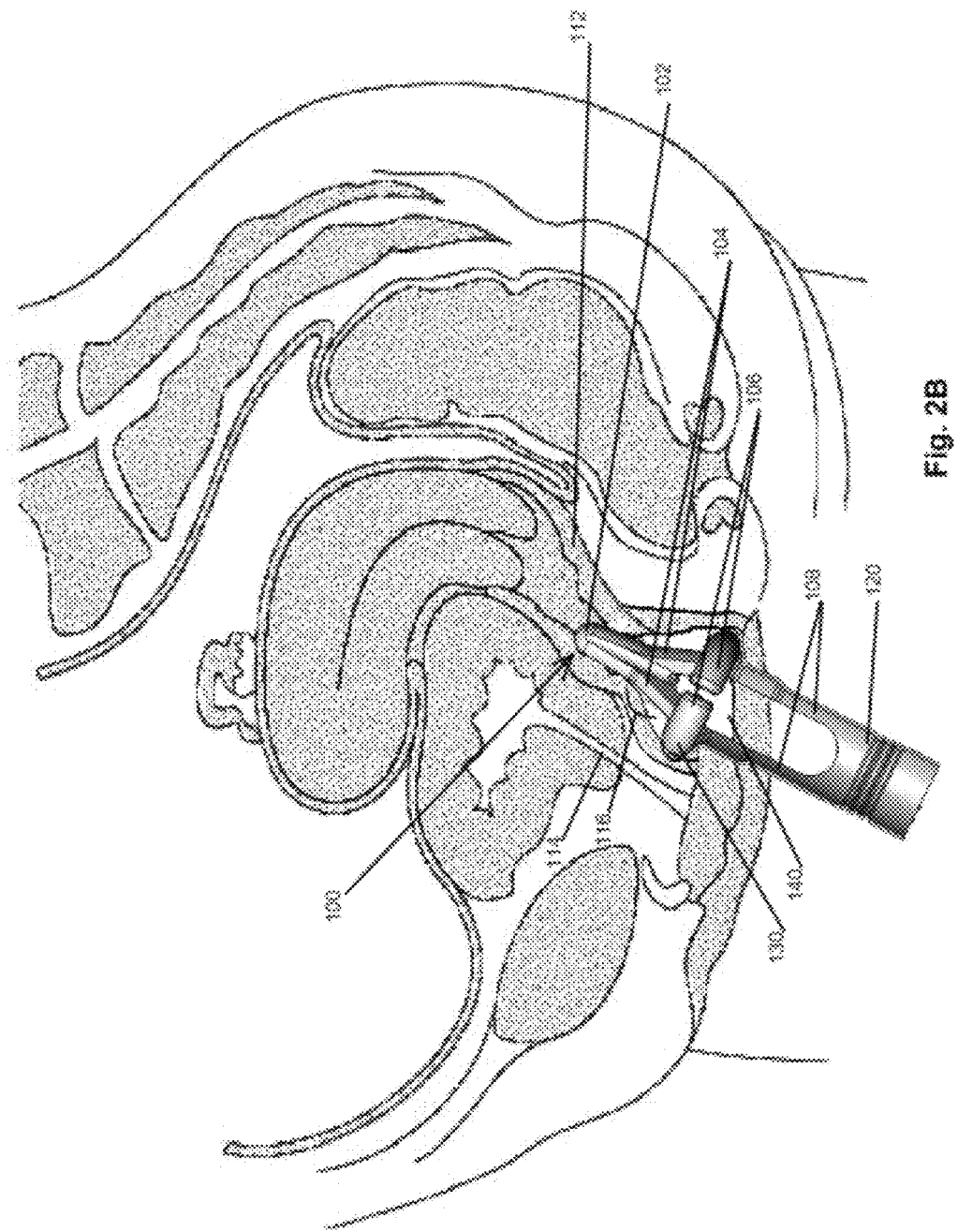

FIGS. 2A-2C show insertion of female urinary incontinence device 100 into a vagina 112. Typically, female urinary incontinence device 100 and vagina 112 are each first lubricated with, for example, a water soluble lubricant.

The labia of the vulva is separated and female urinary incontinence device 100 inserted into vagina 112 using, for example, insertion device 120 and pushed to a position where the incontinence inhibiting device outwardly presses against internal wall of vagina 112 to support a urethra 114 and/or a bladder neck 117. The pressure applied by female urinary incontinence device 100 limits or prevents involuntary passage of urine through urethra 114, thereby inhibiting or preventing female urinary incontinence.

Prongs 108 and round base 130 are typically a flexible material, so that once female urinary incontinence device 100 is in place, friction from vagina 112 holds onto female urinary incontinence device 100, and insertion device 120 can be pulled out of vagina 112 with female urinary incontinence device 100 remaining in place.

In order to remove female urinary incontinence device 100, the labia of the vulva are separated, insertion device 120 is pressed into vagina 112 until prongs 108 grasp the periphery (or internal part) of round base 130 and urinary incontinence device 100 is pulled out of vagina 112.

In some embodiments, insertion device 120 and/or female urinary incontinence device 100 are non-disposable. As in all configurations presented, female urinary incontinence device 100 may be cleaned periodically and used multiple times. Alternatively, female urinary incontinence device 100 may be disposed of and replaced following a single use or even multiple uses.

Urinary incontinence device 100 allows voluntary urination and may be left in place during normal day-to-day activities, overnight and for several days. Urinary incontinence device 100 may be manually inserted, repositioned, and removed by a user; thereby possibly eliminating frequent visits to health care professionals in many cases.

Urinary incontinence device 100 may be manufactured in a plurality of sizes and any number of incontinence inhibiting or prevention devices of varying dimensions could be provided as a set or otherwise.

String Female Urinary Incontinence Devices

Figure 3:
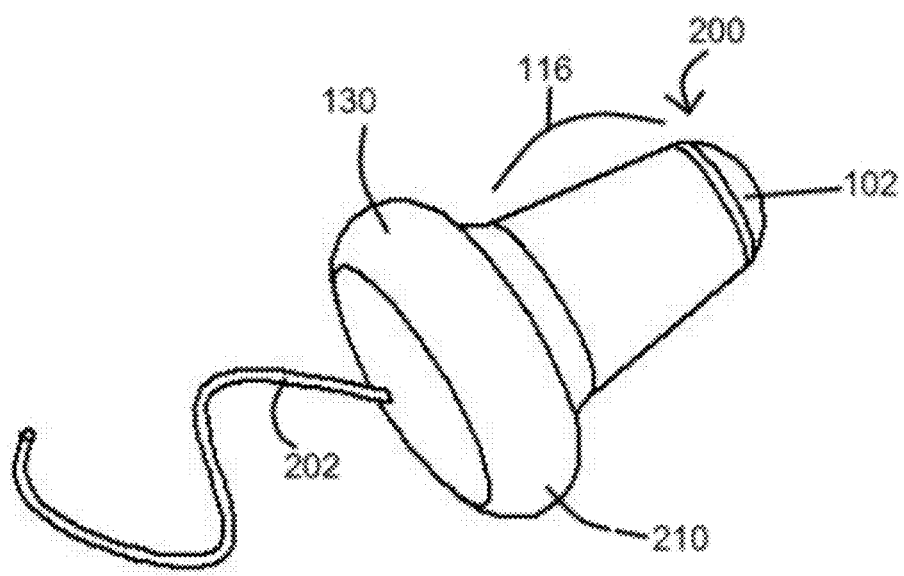
FIGS. 3, 4, 5A and 5B show string insertable female urinary incontinence devices, according to embodiments of the present invention.

FIG. 3 shows a female urinary incontinence device 200 wherein round base 130 comprises a solid disk 210 with an application string 202 extending therefrom.

Application string 202 can be used to assist pulling the female urinary incontinence device 200 during its removal.

Figure 4:
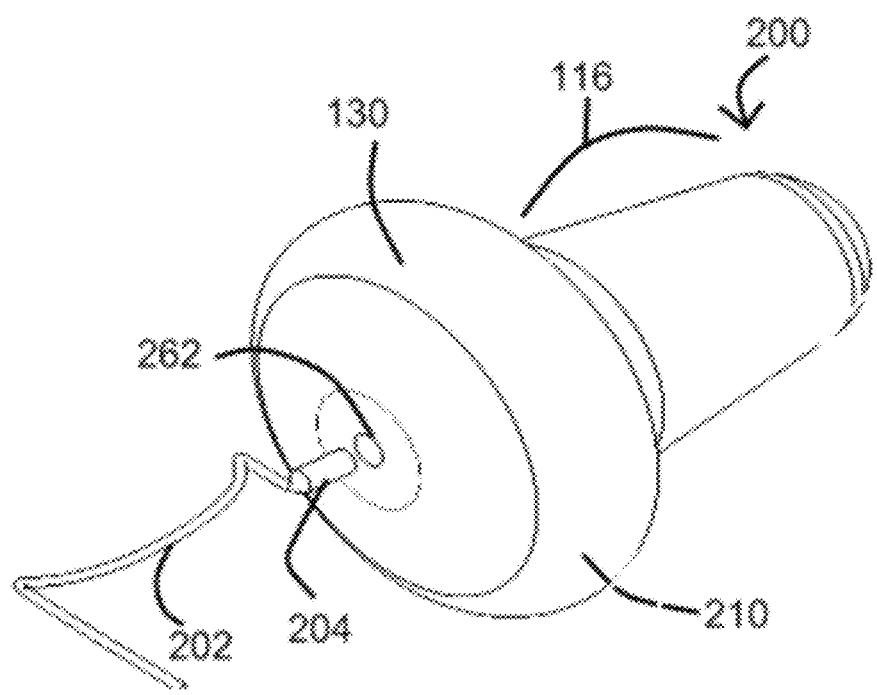

FIG. 4 shows female urinary incontinence device 200 in which application string 202 includes a coupling end 204 that removably inserts into a coupling channel 262, allowing the user to change application string 202 following removal, thereby allowing for use of a fresh string during every use, or periods of use. In embodiments, coupling end 204 may be in have a form of a screw or a drawing pin, referred to as a tucker.

Figure 5A:
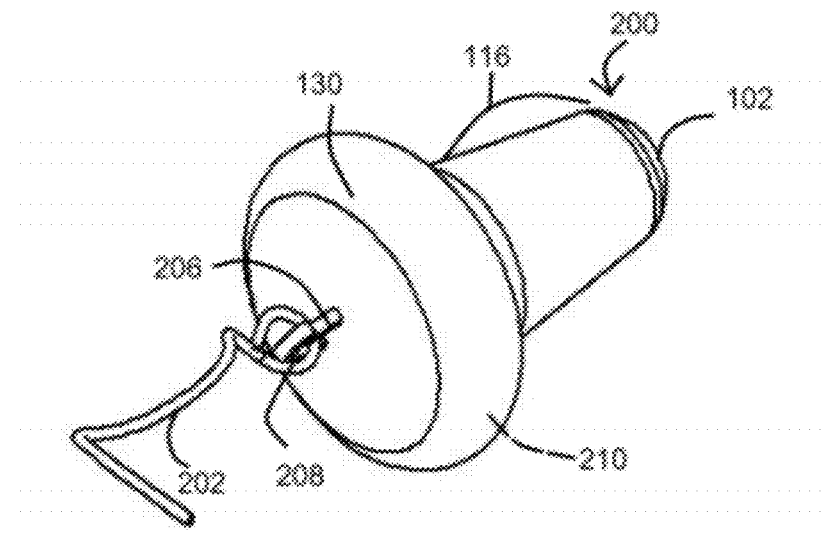
Figure 5B:
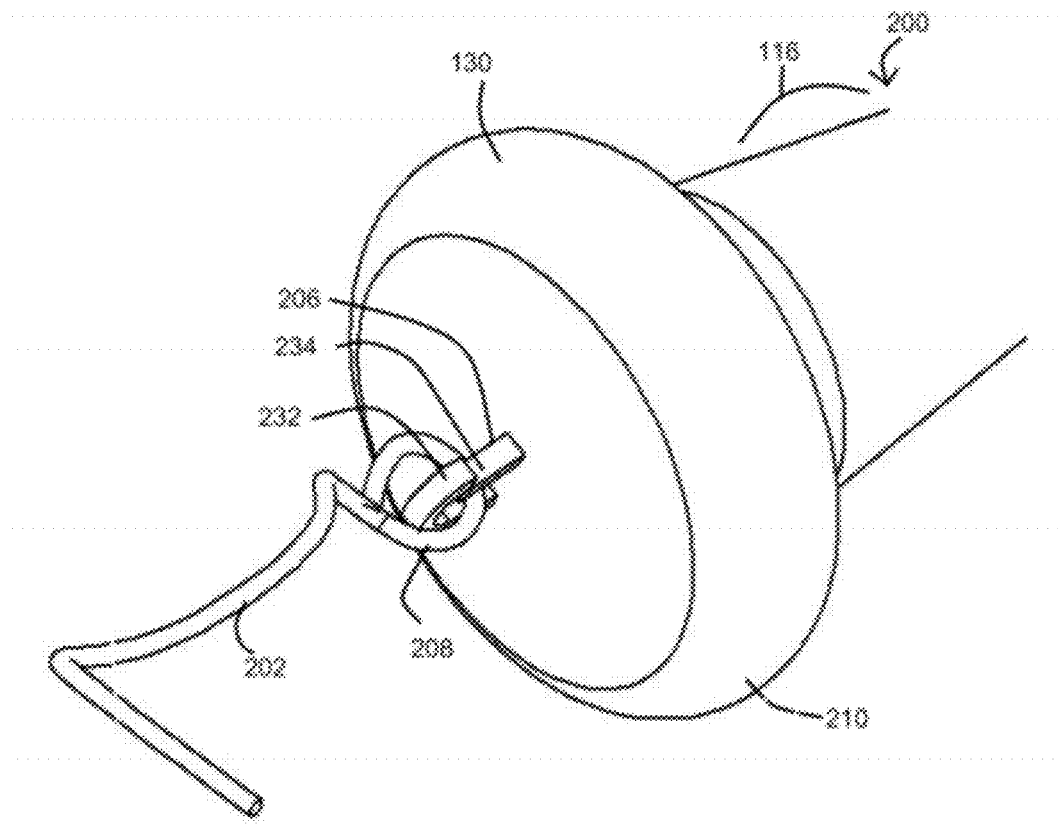

FIGS. 5A-5B show female urinary incontinence device 200 in which application string 202 includes a loop 208 that passes through a latch 206 attached to round base 130. Removal of loop 208 is accomplished by squeezing latch 206 to disengage a post 234 from a hook 232 so that loop 208 can pass through the gap created thereby.

In some instances, a user may prefer using a system including a handle that aids in both insertion and removal of female urinary incontinence device.

Magnetic Female Urinary Incontinence Device and Insertion Device

FIGS. 6A-6B show a system including a magnetic female urinary incontinence device 250 comprising an applicator guide 220 having a magnetic tip 222 and round base 130 including a metal-lined port 224.

During removal of magnetic female urinary incontinence device 250, the user inserts applicator guide 220 near round base 130 and magnetic tip 222 is magnetically guided into port 224.

After magnetic tip 222 is in port 224, the user presses a button 230 that pushes on a hookup rod 238 to grasp port 224 so that magnetic female urinary incontinence device 250 may be removed in spite of the friction of provided by the above-noted tenting.

In some instances, female urinary incontinence device 250, with cone 116 that is solid may cause discomfort to some users and/or prevent a user from inserting a finger to guide female urinary incontinence device 250 into place. A variety of flexible and/or hollow configurations of female urinary incontinence device 250 are presented herein.

Hollow Female Urinary Incontinence Device

Figure 7A:
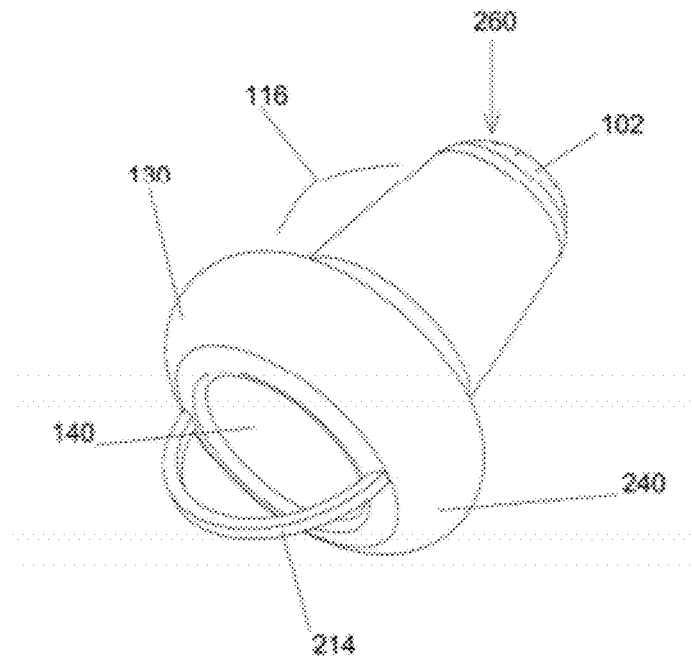
FIGS. 7A, 7B, 8A, 8B and 8C show a hollow female urinary incontinence device and an insertion device, according to embodiments of the present invention.
Figure 7B:
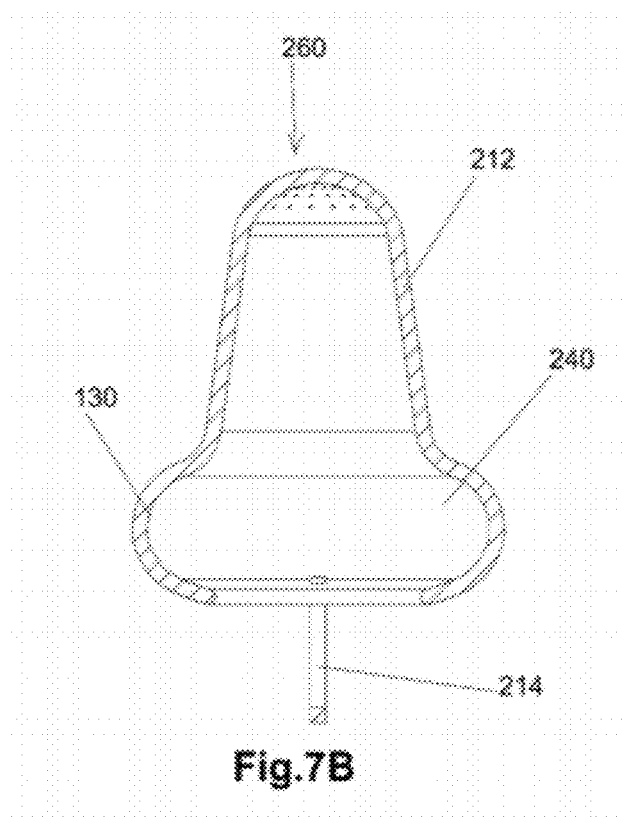

FIGS. 7A-7B show a hollow female urinary incontinence device 260 wherein round base 130 comprises a wall 240 that is hollow to reduce rigidity and possibly increase user comfort. Additionally or alternatively, cone portion 130 may comprise hollow wall 240 to further increase user comfort.

Additionally, hollow female urinary incontinence device 260 optionally includes a low bulk application ring 214 that is easily grasped by the user during application.

In some instances a user may prefer using an insertion device with hollow female urinary incontinence device 260, while using low bulk application ring 214 for removal; and the following embodiments are presented to possibly satisfy this preference.

Insertion Device for Hollow Female Urinary Incontinence Device

Figure 8C:
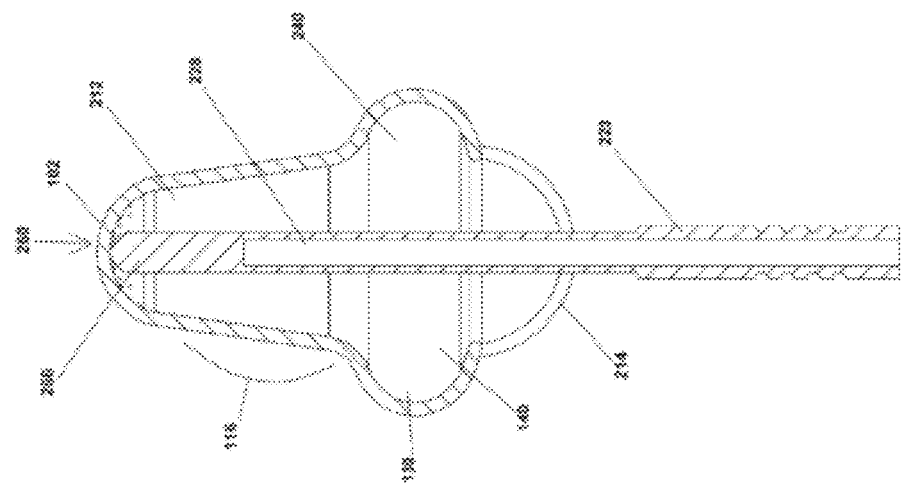
Figure 8B:
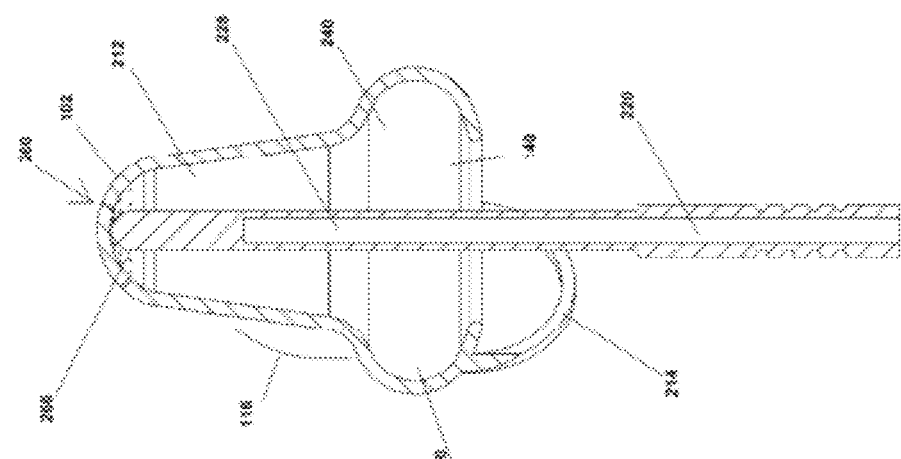
Figure 8A:
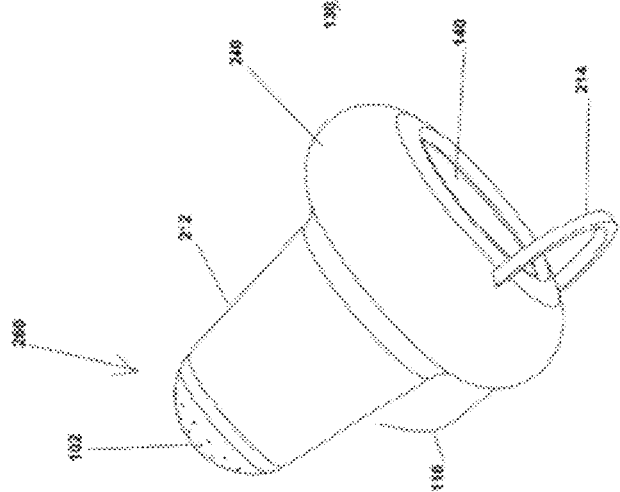

FIGS. 8A-8C show insertion handle 220 having a coupling end 228 that inserts into a coupling channel 266 of hollow female urinary incontinence device 260.

Following positioning of hollow female urinary incontinence device 260, insertion handle 220 is pulled to slide coupling end 220 out of coupling channel 266.

To accommodate the axial position of coupling end 228, low bulk application ring 214 has been moved off-center to the longitudinal axis of hollow female urinary incontinence device 260.

In some embodiments, hollow female urinary incontinence device 260 includes round base 130 comprising a torus having an inner diameter that is large enough to fit on an index finger. In such configurations, hollow female urinary incontinence device 260 may be pushed into place, aligned and/or removed while sitting on the index finger.

Some users may prefer using a device to remove hollow female urinary incontinence device 260 rather than directly grasping application ring 214; the following embodiment address this preference:

Removal Device for Hollow Female Urinary Incontinence Device

FIG. 9 shows a removal handle 225 including a hook 245 that is coupled to low bulk application ring 214 and can be used to easily remove hollow female urinary incontinence device 260 from the user.

Blocking the flow of vaginal secretions may present a problem during use of female urinary incontinence devices. The following embodiments address such issues:

Secretion Aiding Female Urinary Incontinence Insertion Devices

Figure 10A:
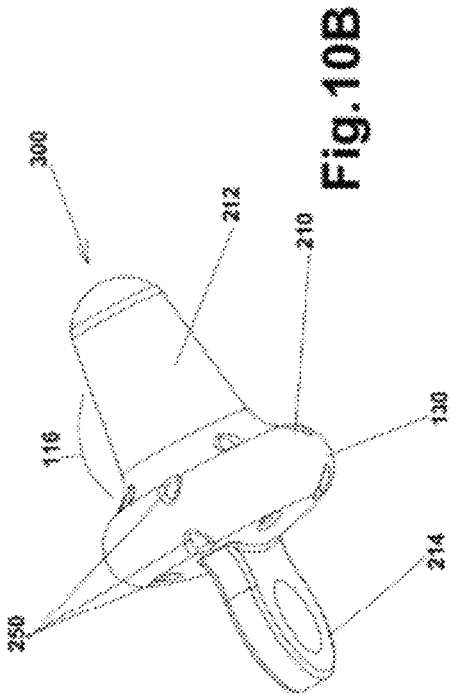
FIGS. 10A, 10B, 10C and 10D show alternative configurations of female urinary incontinence devices, according to embodiments of the present invention.
Figure 10B:
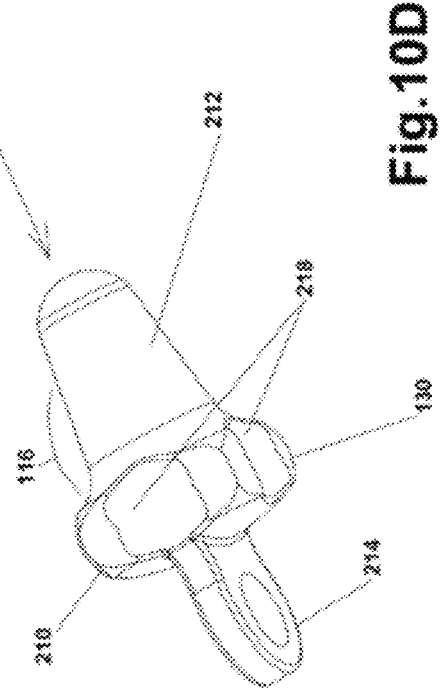

FIGS. 10A-10B show a female urinary incontinence device 300 comprising secretion passages 251 in round base 130 that is substantially solid. Secretion passages 251 are of a size that allows passage of female secretions.

Figure 10C:
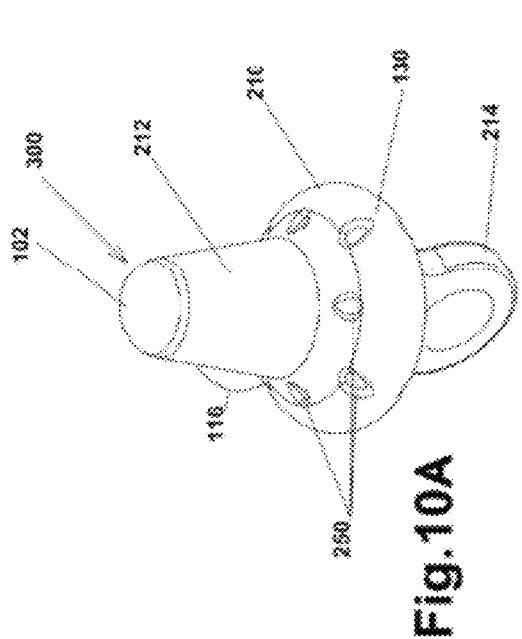
Figure 10D:
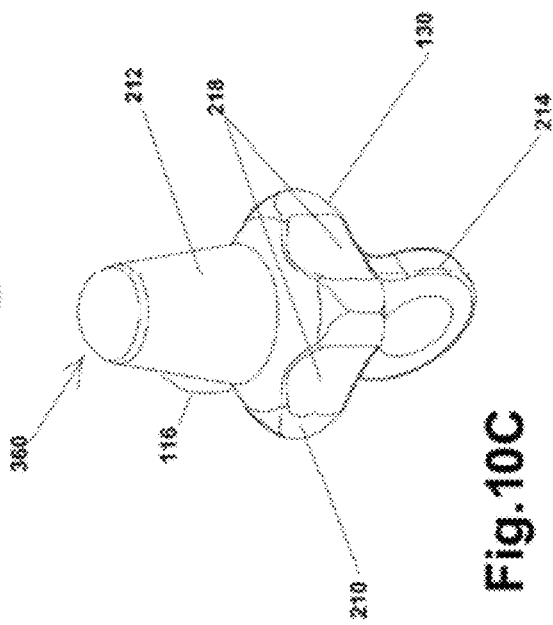

FIGS. 10C-10D show a female urinary incontinence device 360 comprising secretion grooves 218 in round base 130 for allowing passage of female secretions.

In some instances, a user may have exceptionally weak musculature that, unfortunately, allows displacement or expulsion of female urinary incontinence insertion device 360, for example during a sneeze or cough. The following embodiments provide an anchoring configuration that addresses such displacement problems.

Anchoring Female Urinary Incontinence Devices

Figure 11A:
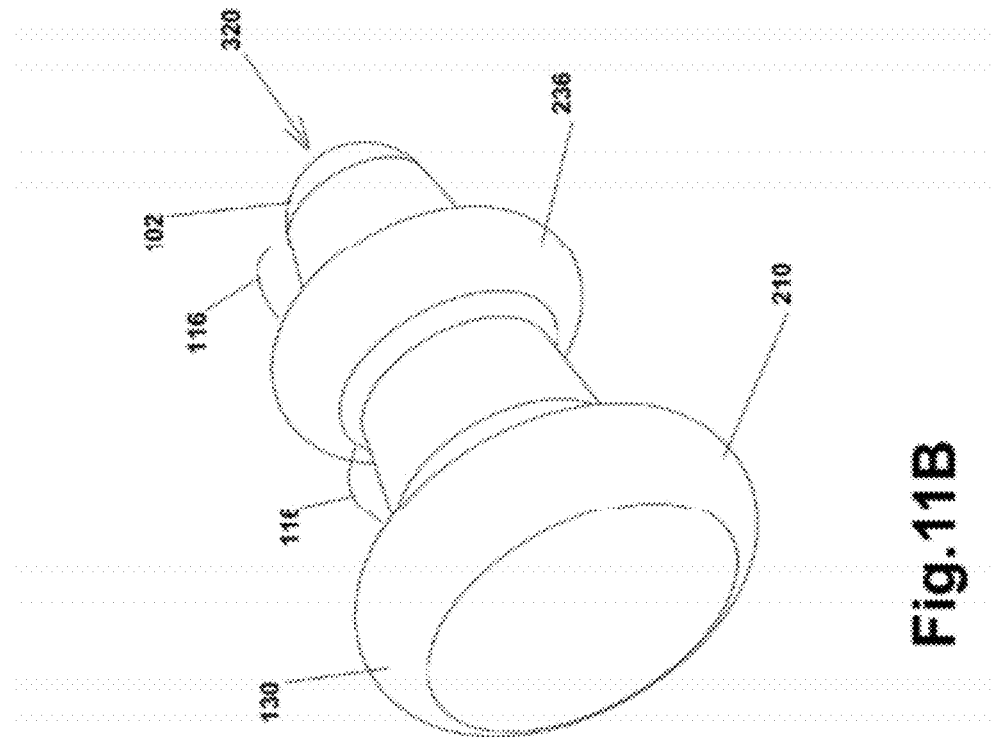
FIGS. 11A-11B show an anchoring configuration of a female urinary incontinence device, according to embodiments of the present invention.
Figure 11B:
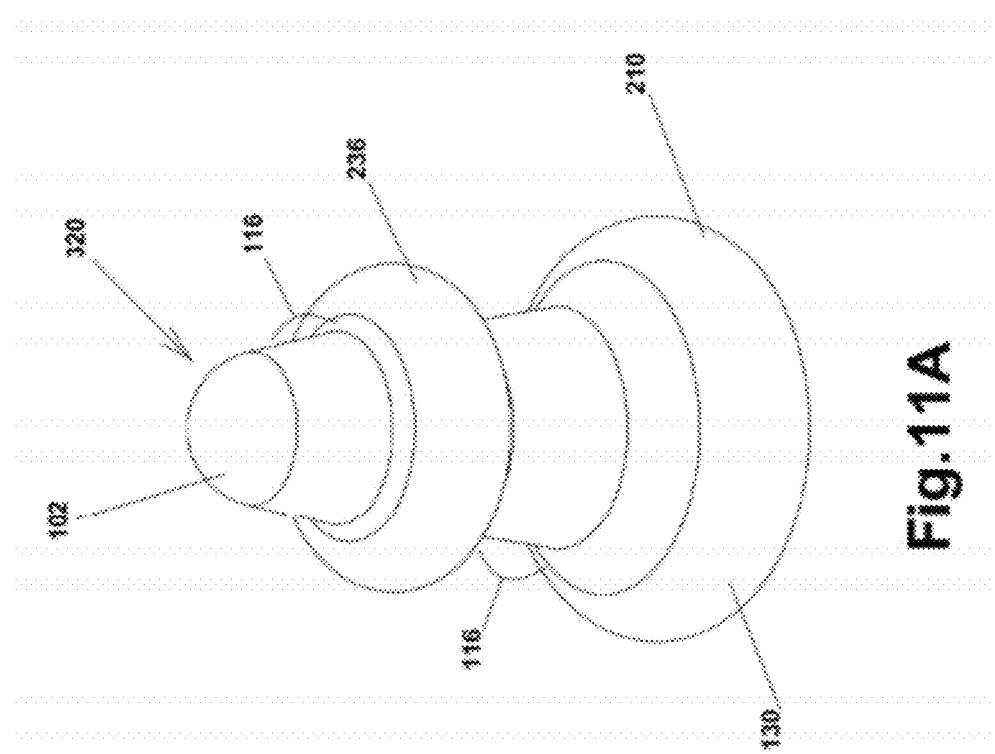

FIGS. 11A-11B show an anchoring female urinary incontinence device 320 comprising a solid anchor ring 236 along cone 116 which is solid as well. Solid anchor ring 236 provides additional friction against vaginal wall 112 as seen in FIG. 2C, so that the tenting effect of vaginal wall is pronounced, thereby providing increased anchoring.

Open Prong Female Urinary Incontinence Device

Figure 12A:
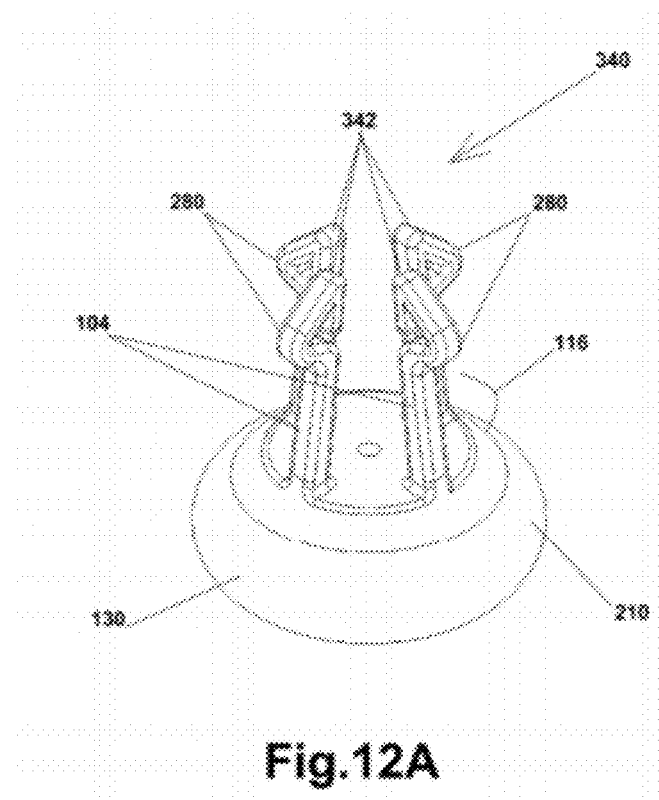
FIGS. 12A, 12B, 13, 14, 15, 16, 17, 18A, 18B, 19A, 19B, 20A, 20B, 21A and 21B show alternative configurations of female urinary incontinence devices, according to embodiments of the present invention.
Figure 12B:
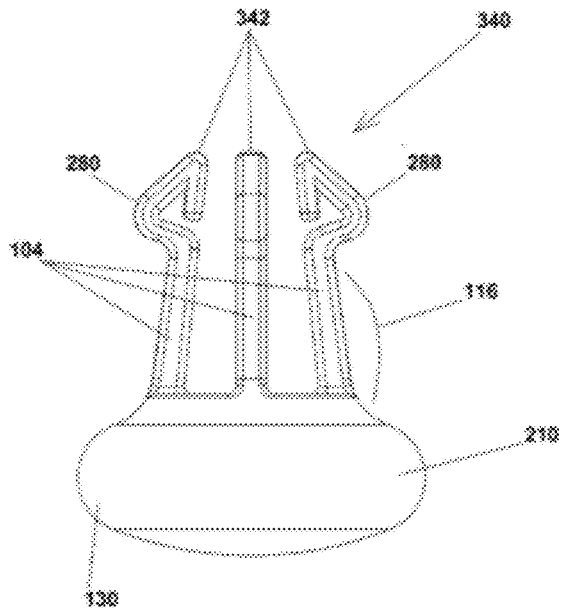
Figure 13:
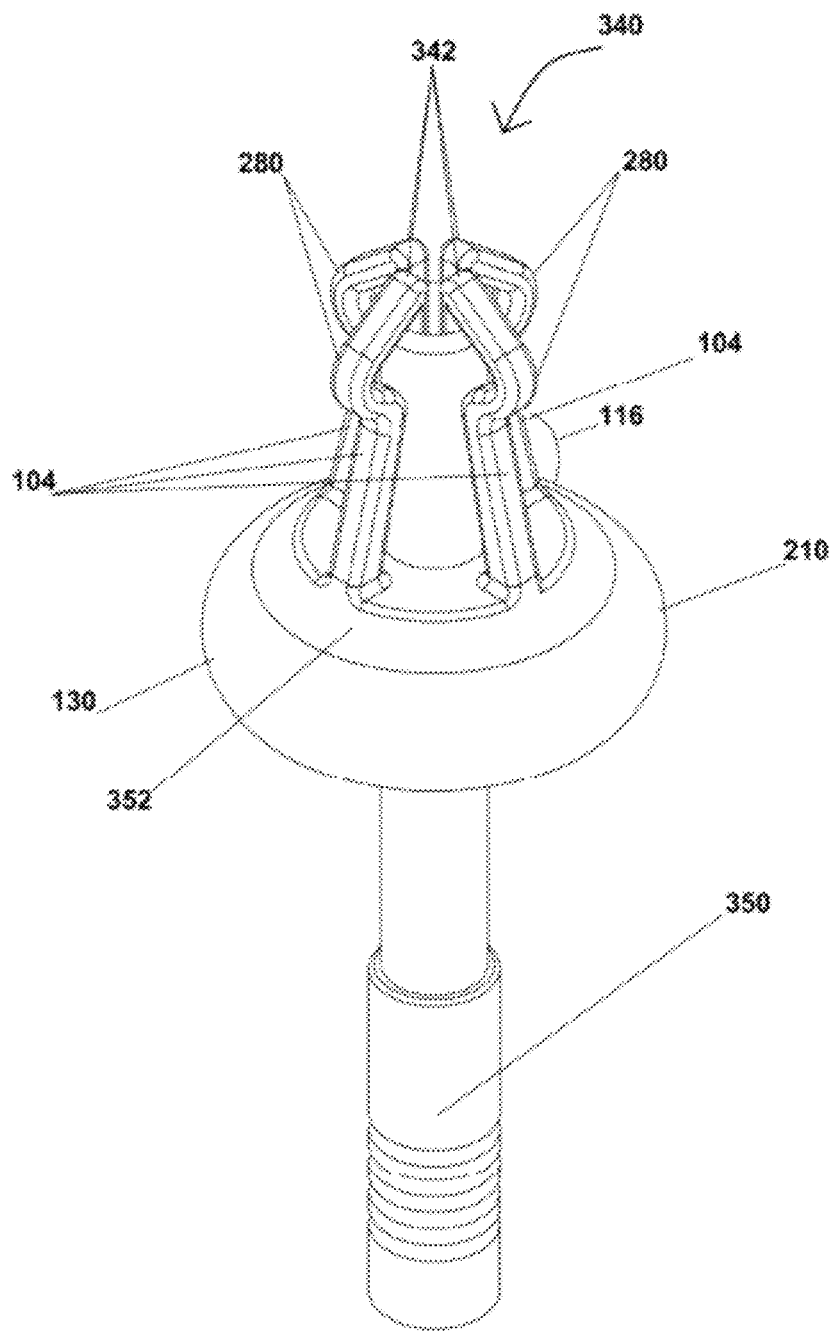

FIGS. 12A-13 show an open prong female urinary incontinence device 340 in which posts 104 are resilient and free standing, meaning unattached, for example, to nose 102 (FIG. 1A). Additionally, each of posts 104 include an upper curvature 280 that extends radially outward. Upper curvatures 280 extend into vaginal walls 112 (FIG. 2C) to provide increased resistance against displacement.

As seen in FIG. 12B, control prongs 342 are spaced a distance from the longitudinal axis of female urinary incontinence device 340.

As seen in FIG. 13, when open prong female urinary incontinence device 340 is loaded on an inserter handle 350, control prongs 342 are pushed into an inserter tube, thereby reducing the distance between control prongs and causing posts 104 to resiliently bend radially inwardly, hence forming a compact end that facilitates easy and smooth insertion.

Following insertion, inserter handle 350 is removed, freeing control prongs 342 from an inserter tube 352 allowing posts 104 to resiliently bend radially outward. The outward thrust of posts 104 presses against the tenting configuration of vaginal walls 112 (FIG. 2C), thereby increasing friction and resistance against displacement.

In some instances, a user might prefer a device that, similar to open prong female urinary incontinence device 340, takes advantage of tenting configuration, but does not include posts 104 that resiliently bend radially outward.

Closed Prong Female Urinary Incontinence Device

Figures 14, 15:
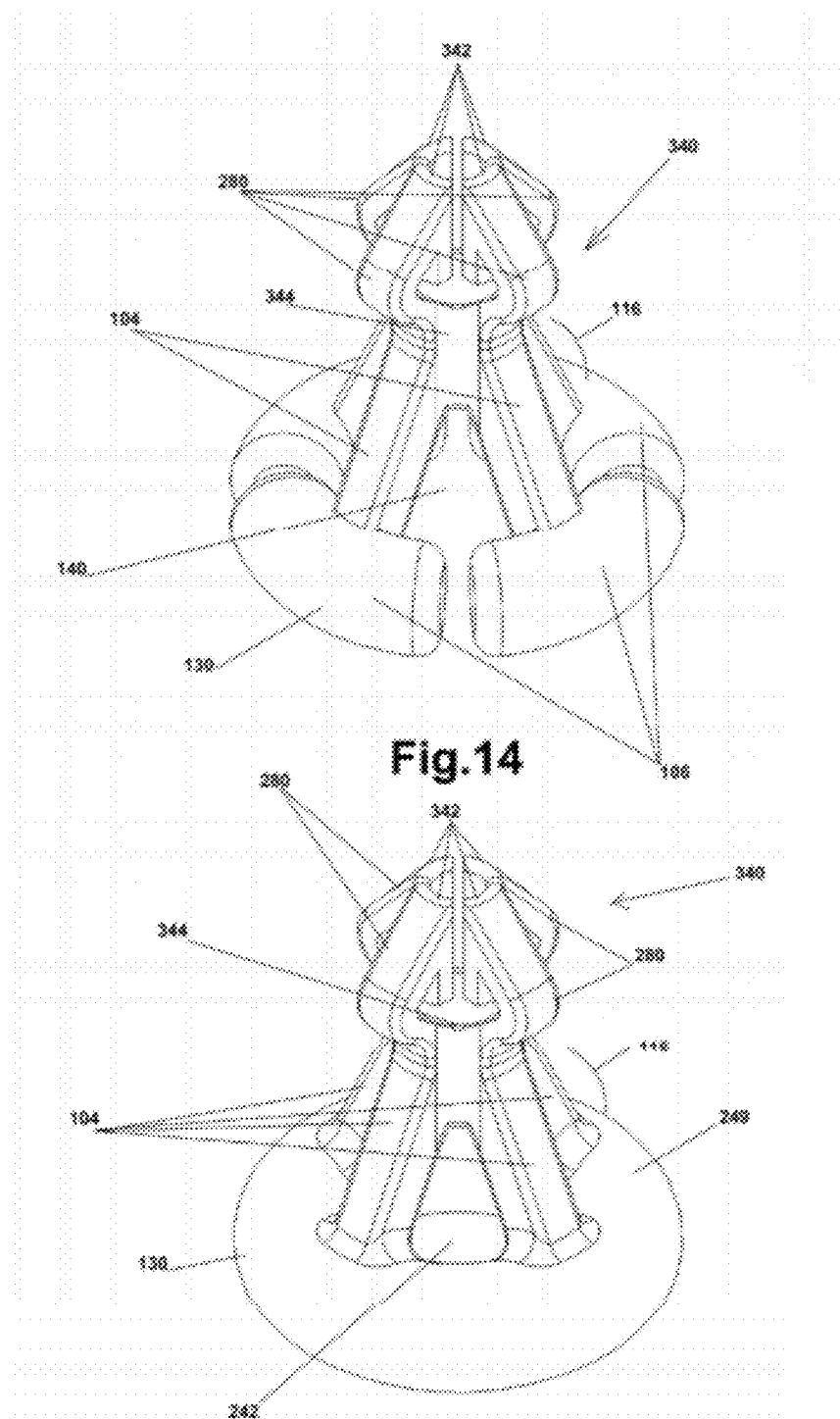
Figure 16:
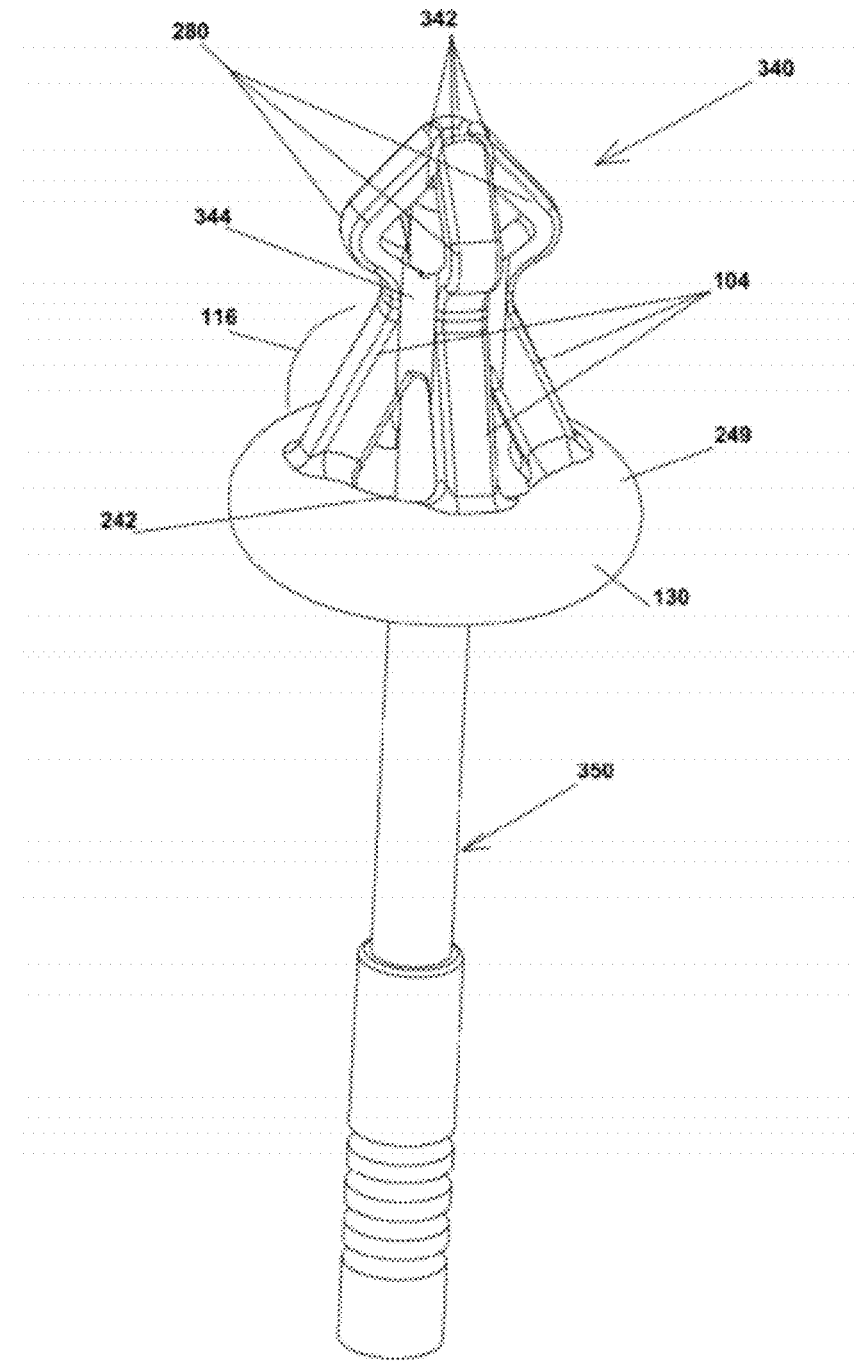

FIGS. 14-16 show closed prong female urinary incontinence devices 340 in which posts 104 are joined at a core 344, thereby facilitating insertion and preventing radially outward movement of posts 104, and providing increased friction to resist displacement.

FIG. 14 shows closed prong female urinary incontinence device 340 including multiple semi-circular sections 106.

FIG. 15 shows closed prong female urinary incontinence device 340 including a solid torus 249 surrounding an instrument insertion cavity 242, while FIG. 16 shows an inserter handle 350 passing through instrument insertion cavity 242 prior to application.

Figure 17:
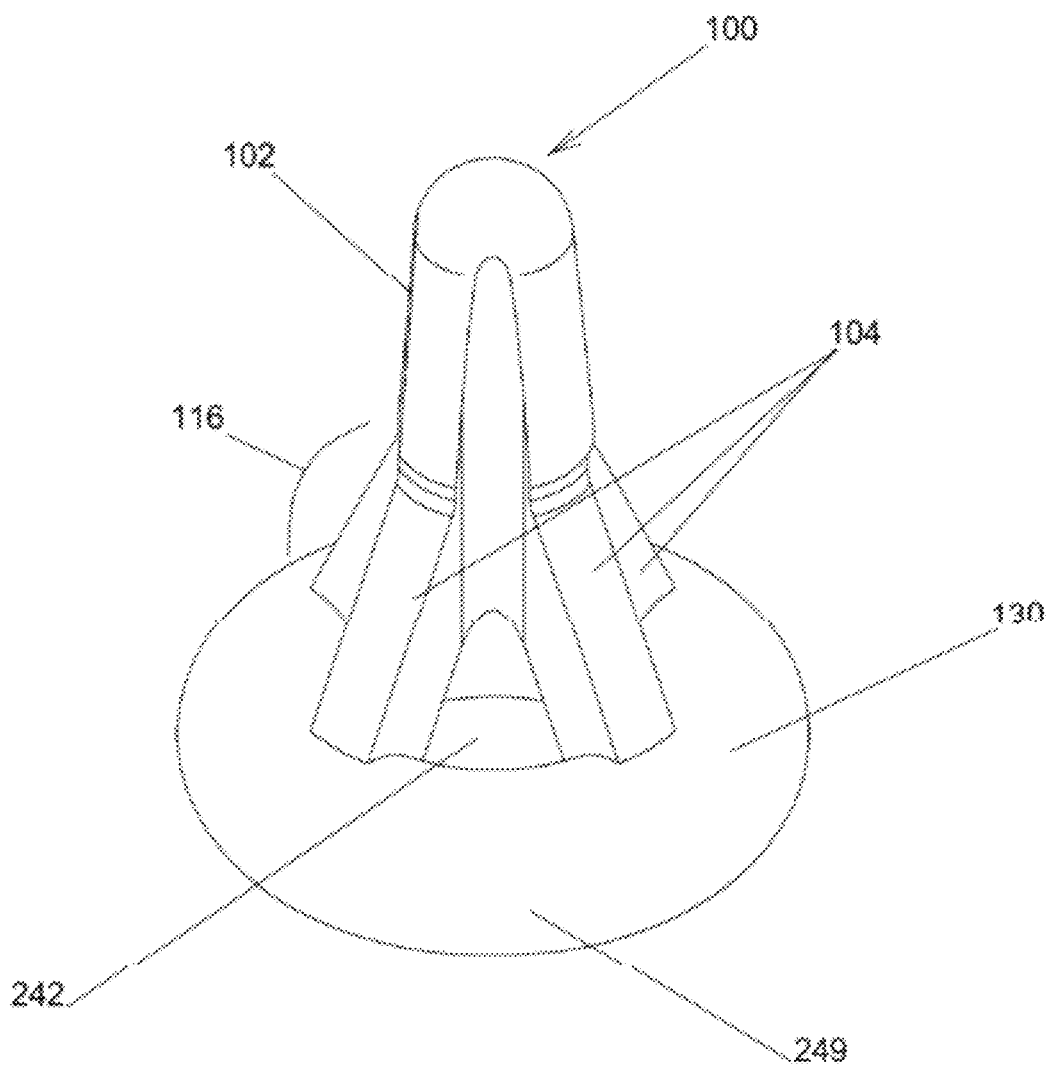

FIG. 17 shows female urinary incontinence device 100 including solid torus 249 surrounding instrument insertion cavity 242.

There are many additional configurations of female urinary incontinence devices that may be preferred by users due to ease of insertion and/or removal or even aesthetic considerations; and the following embodiments address such preferences:

Alternative Configurations of Female Urinary Incontinence Devices

FIGS. 18A-21B show alternative configurations of guiding devices for female urinary incontinence device 100.

Figure 18A:
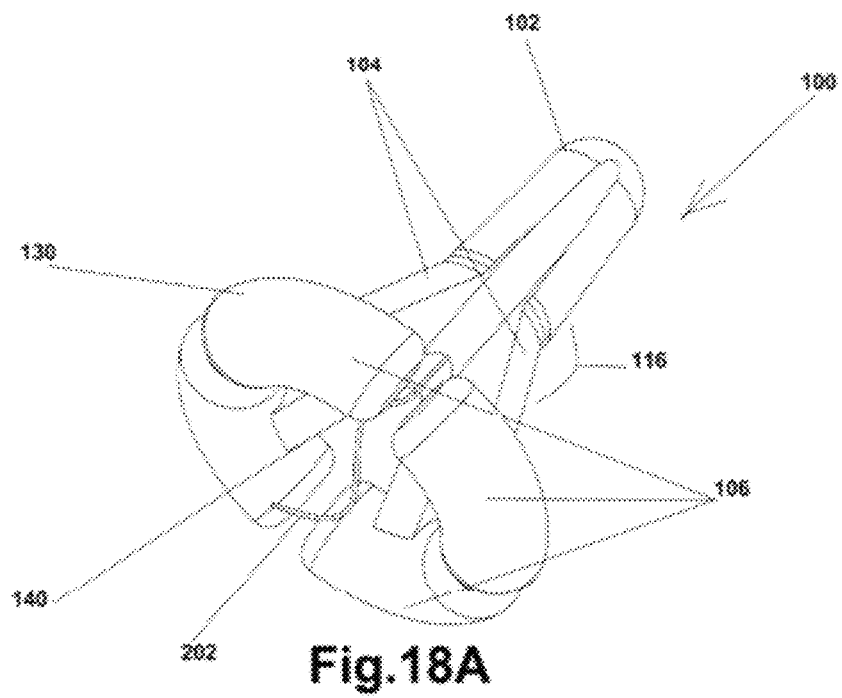
Figure 18B:
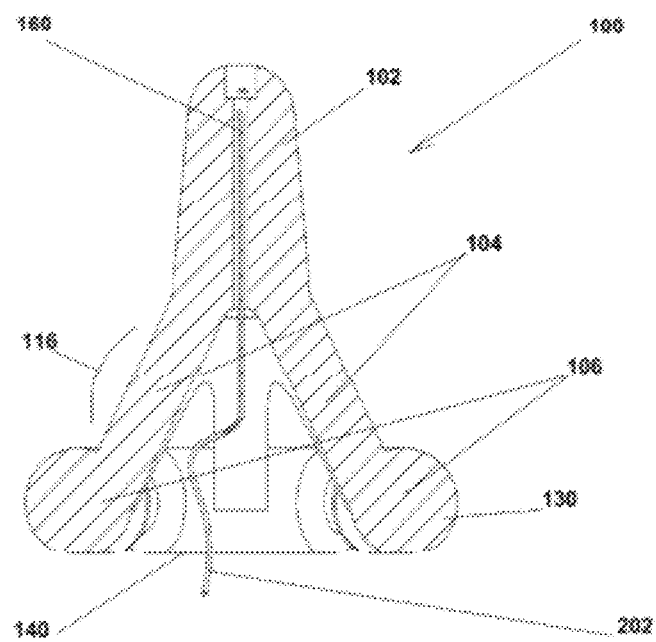

FIGS. 18A-18B show string 202 anchored in a string channel 160 that passes through blunt nose 102 and cone 116 and exits through cavity 140 between multiple semi-circular sections 106. String channel 160 serves to center string 202 so that string may pass through a hollow instrument, for example inserter tube 352 and handle 350 (FIG. 13) to stabilize female urinary incontinence device 100 during insertion.

In some embodiments, string 202 may be removably attached in string channel 160 to allow the user to easily change string 202 when so desired. In further embodiments, the user may optionally insert female urinary incontinence device 100 without string 202.

Figure 19A:
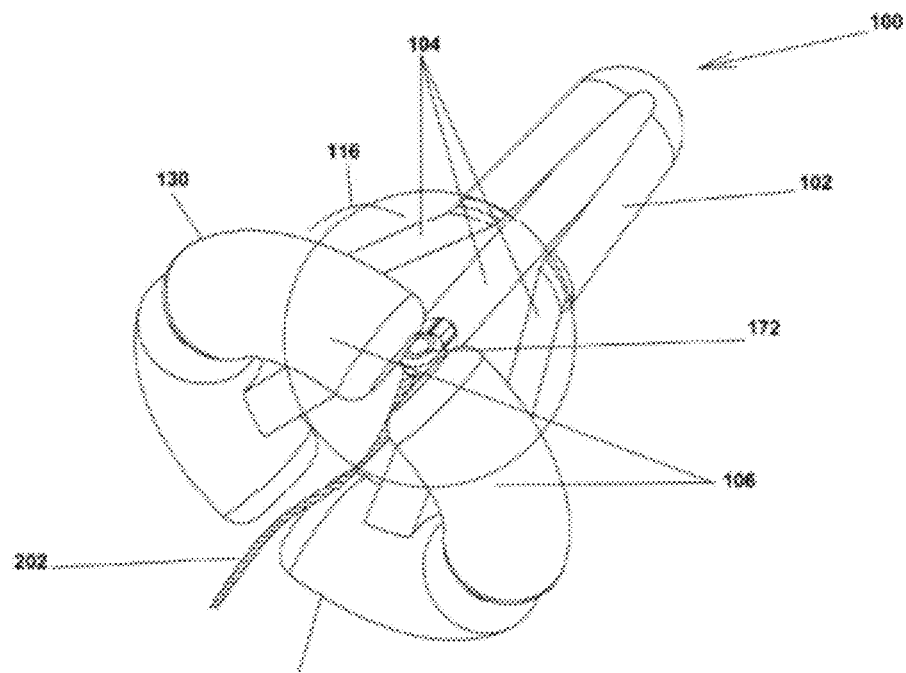
Figure 19B:
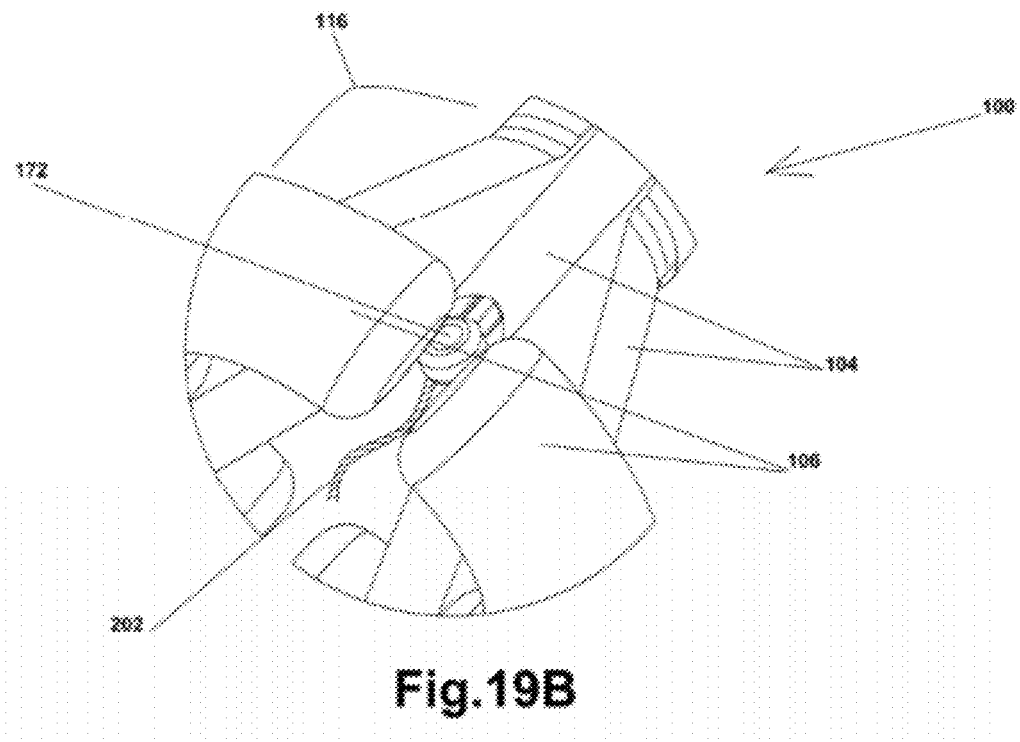

FIGS. 19A-19B show an anchor button 172 projection to which application string 202 is attached.

Figure 20A:
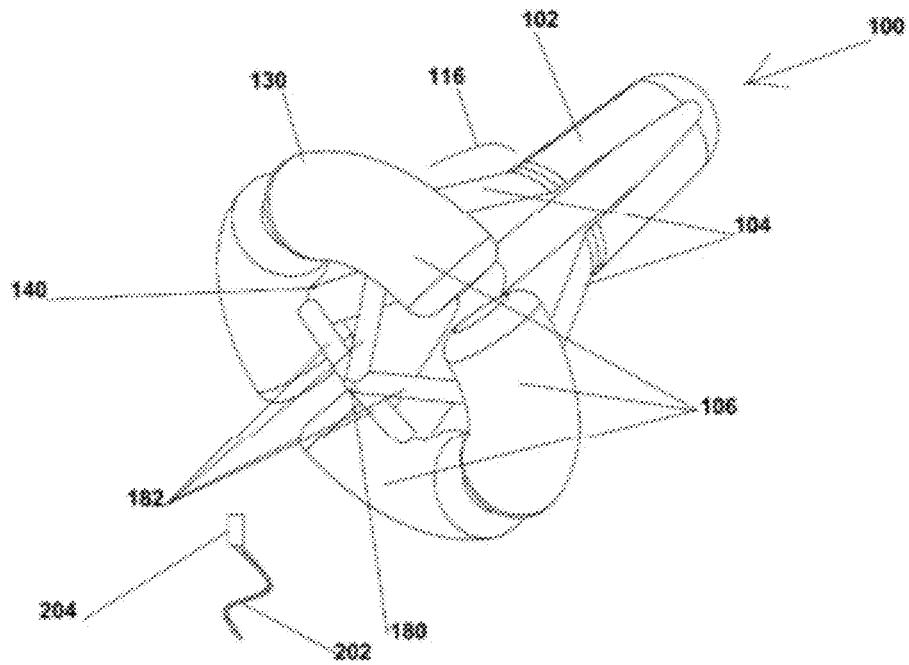
Figure 20B:
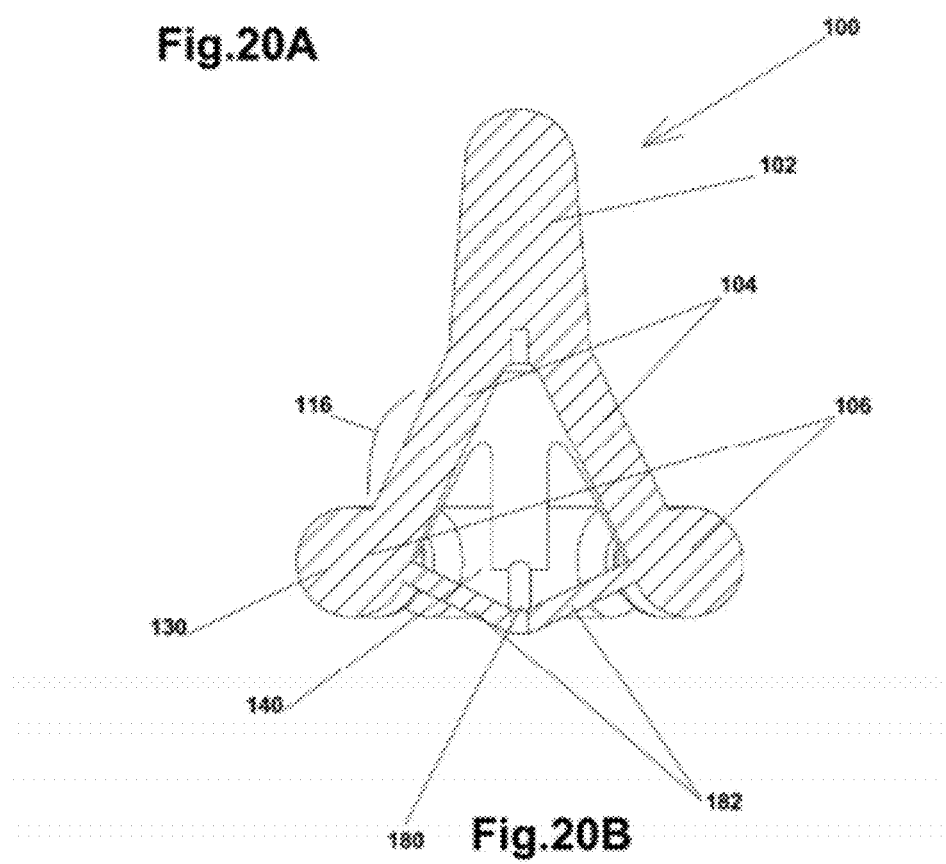

FIGS. 20A-20B show coupling end 204 that inserts into a coupling passage 180 between multiple spokes 182 to anchor string 202 to female urinary incontinence device 100.

Figure 21A:
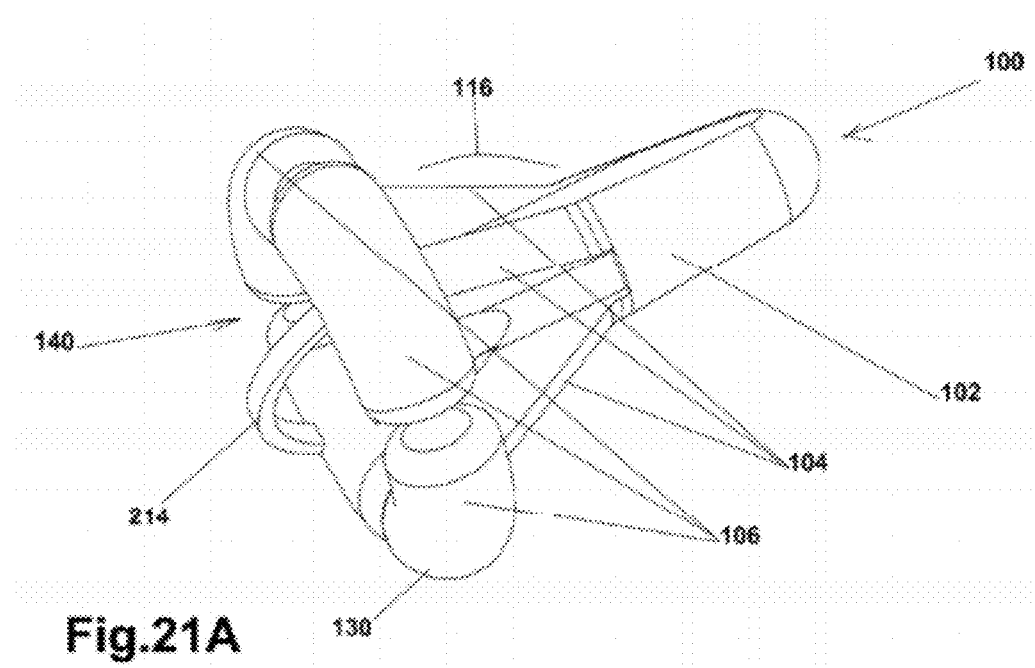
Figure 21B:
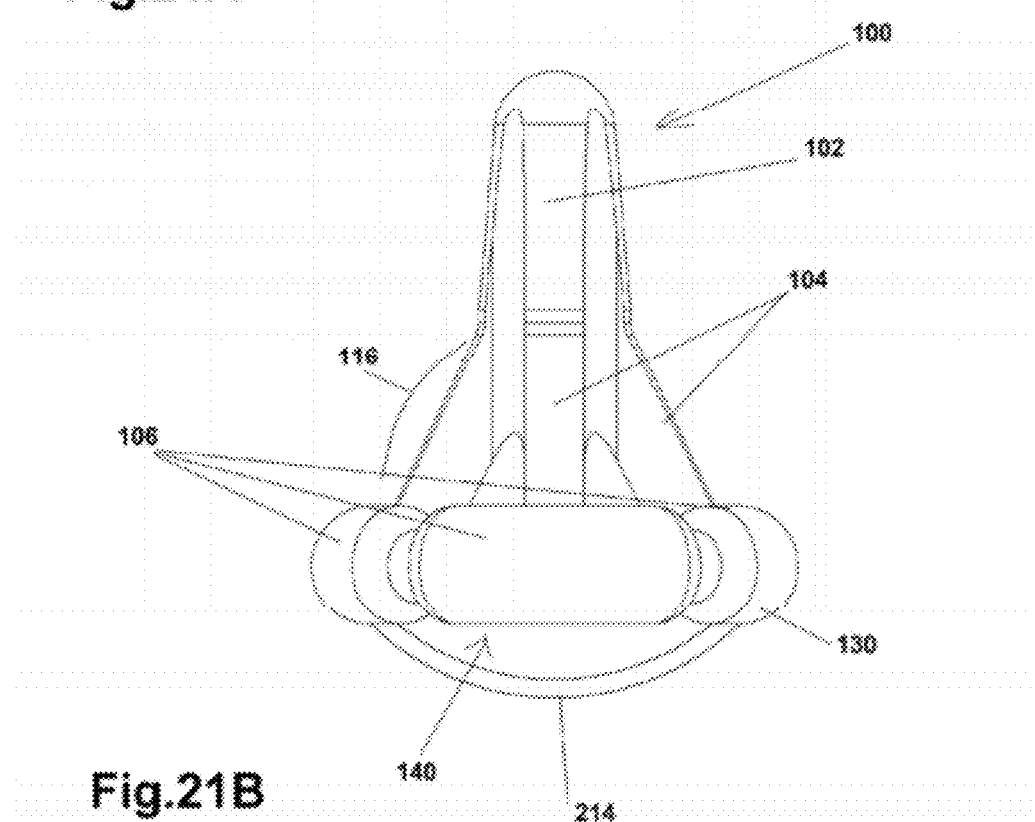

FIGS. 21A-21B show female urinary incontinence device 100 with low bulk application ring 214.

It is expected that during the life of a patent maturing from this application many relevant female urinary incontinence devices will be developed and the scope of the term female urinary incontinence device is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A female urinary incontinence-inhibiting device, comprising;
   i) a torus comprising multiple semi-circular sections, centered around and encircling a longitudinal axis of the device, having a diameter configured to inhibit female urinary incontinence when placed in a vagina; and
   ii) a generally tapering stabilizing element, coupled to said torus symmetrically around the longitudinal axis, said stabilizing element extending away from the torus and radially inward to form a cone shape, said stabilizing element having a size and position configured to stabilize said torus within the vagina without using suction, wherein said torus comprises at least one unobstructed slot therethrough which divides one of the semi-circular sections from another of the semi-circular sections, said at least one slot having an average cross section diameter sufficient to allow passage of female secretions when said device is positioned in a vagina.

2. The device according to claim 1, wherein said at least one unobstructed slot comprises a groove in said torus.

3. The device according to claim 1, wherein said torus is a flexible torus and the at least one slot is configured to, under compression, flexibly reduce the outer diameter of said torus for insertion into the vagina.

4. The device according to claim 1, including a cavity of sufficient size to allow insertion of an average finger of a female.

5. The device according to claim 4, wherein a center of said cavity is aligned with the axial axis of said torus.

6. The device according to claim 1, wherein said stabilizing element comprises at least two flexible posts.

7. The device according to claim 1, further comprising a string channel through a central axis of the stabilizing element.

8. The device according to claim 7, further comprising a string anchored in the string channel at an end of the stabilizing element away from the torus, where the string extends down the string channel and past the torus.

9. The device according to claim 8, wherein the string is removably attached to the string channel.

10. A kit for inserting a female urinary incontinence-inhibiting device, comprising:
   the device according to claim 8; and
   a hollow inserter tube adapted for passage of the string therethrough and adapted to be removably positioned in a cavity of the device for inserting the device into a vagina.

\* \* \* \* \*